(12) United States Patent
Schecter

(10) Patent No.: US 7,010,347 B2
(45) Date of Patent: Mar. 7, 2006

(54) OPTIMIZATION OF IMPEDANCE SIGNALS FOR CLOSED LOOP PROGRAMMING OF CARDIAC RESYNCHRONIZATION THERAPY DEVICES

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/860,990

(22) Filed: Jun. 4, 2004

(65) Prior Publication Data

US 2005/0182447 A1    Aug. 18, 2005

Related U.S. Application Data

(63) Continuation-in-part of application No. 10/779,162, filed on Feb. 14, 2004.

(51) Int. Cl.
*A61N 1/365* (2006.01)

(52) U.S. Cl. .......................................... 607/17; 607/9

(58) Field of Classification Search ............ 607/17–18, 607/28, 4–6, 8–9, 30, 32
See application file for complete search history.

(56) References Cited

U.S. PATENT DOCUMENTS

| | | | |
|---|---|---|---|
| 5,183,040 A | 2/1993 | Nappholz et al. | 128/419 PG |
| 5,213,098 A | 5/1993 | Bennett et al. | 128/419 PG |
| 5,792,197 A * | 8/1998 | Nappholz | 607/17 |
| 6,070,100 A | 5/2000 | Bakels et al. | 607/9 |
| 6,539,261 B1 | 3/2003 | Dal Molin | 607/20 |
| 6,628,988 B1 | 9/2003 | Kramer et al. | 607/9 |
| 6,704,600 B1 | 3/2004 | Daum | 607/30 |
| 6,708,061 B1 | 3/2004 | Salo et al. | 607/9 |
| 6,725,091 B1 | 4/2004 | Dal Molin | 607/2 |
| 6,760,623 B1 | 7/2004 | Stahmann et al. | 607/9 |
| 6,795,733 B1 * | 9/2004 | Lu | 607/17 |
| 6,832,113 B1 | 12/2004 | Belalcazar | 607/23 |
| 2002/0002389 A1 | 1/2002 | Bradley et al. | 607/8 |
| 2003/0204212 A1 * | 10/2003 | Burnes et al. | 607/17 |
| 2004/0010293 A1 | 1/2004 | Holmstrom et al. | 607/9 |
| 2004/0015081 A1 | 1/2004 | Kramer et al. | 600/439 |
| 2004/0030356 A1 | 2/2004 | Osypka | 607/17 |
| 2004/0049235 A1 | 3/2004 | Deno et al. | 607/9 |
| 2004/0186524 A1 | 9/2004 | Chinchoy | 607/17 |
| 2004/0215252 A1 | 10/2004 | Verbeck et al. | 607/9 |
| 2004/0220636 A1 * | 11/2004 | Burnes | 607/17 |
| 2004/0220637 A1 | 11/2004 | Zdeblick et al. | 607/17 |
| 2004/0230239 A1 | 11/2004 | Stahmann et al. | 607/14 |
| 2004/0243192 A1 | 12/2004 | Hepp et al. | 607/17 |
| 2005/0027320 A1 | 2/2005 | Nehls et al. | 607/9 |
| 2005/0038481 A1 | 2/2005 | Chinchoy et al. | 607/17 |

FOREIGN PATENT DOCUMENTS

WO    WO 2004/050177 A1 *   6/2004

* cited by examiner

*Primary Examiner*—Carl H. Layno

(57) ABSTRACT

What are described herein are implantable cardiac devices such as pacemakers and defibrillators that deliver cardiac resynchronization therapy (CRT), and to a method of optimizing acquisition of impedance signals between electrodes present on implanted lead systems. This system then automatically determines which electrodes or electrode combinations acquire impedance waveforms that have the best signal to noise ratio (highest fidelity) and characterize data most representative of dysynchronous electro-mechanical events. Using closed loop algorithms which provide electrograms and a variety of impedance data reflective of the patient's clinical status, the system autonomously modifies interval timing within the CRT device.

15 Claims, 33 Drawing Sheets

Figure 5

| | Systolic integrals of Z(t)dt | Diastolic integrals of Z(t)dt | Identification of valvular event timing / morphology | Line Integrals of Z(t)dt |
|---|---|---|---|---|
| Maximal Signal Fidelity | | | | |
| Intermediate Signal Fidelity | Z (peak) | dZ/dt | dZ'/dt | dZ"/dt |
| Least Signal Fidelity | Time of onset of Z(t) | Time of peak dZ/dt | Time of Z(peak) | |

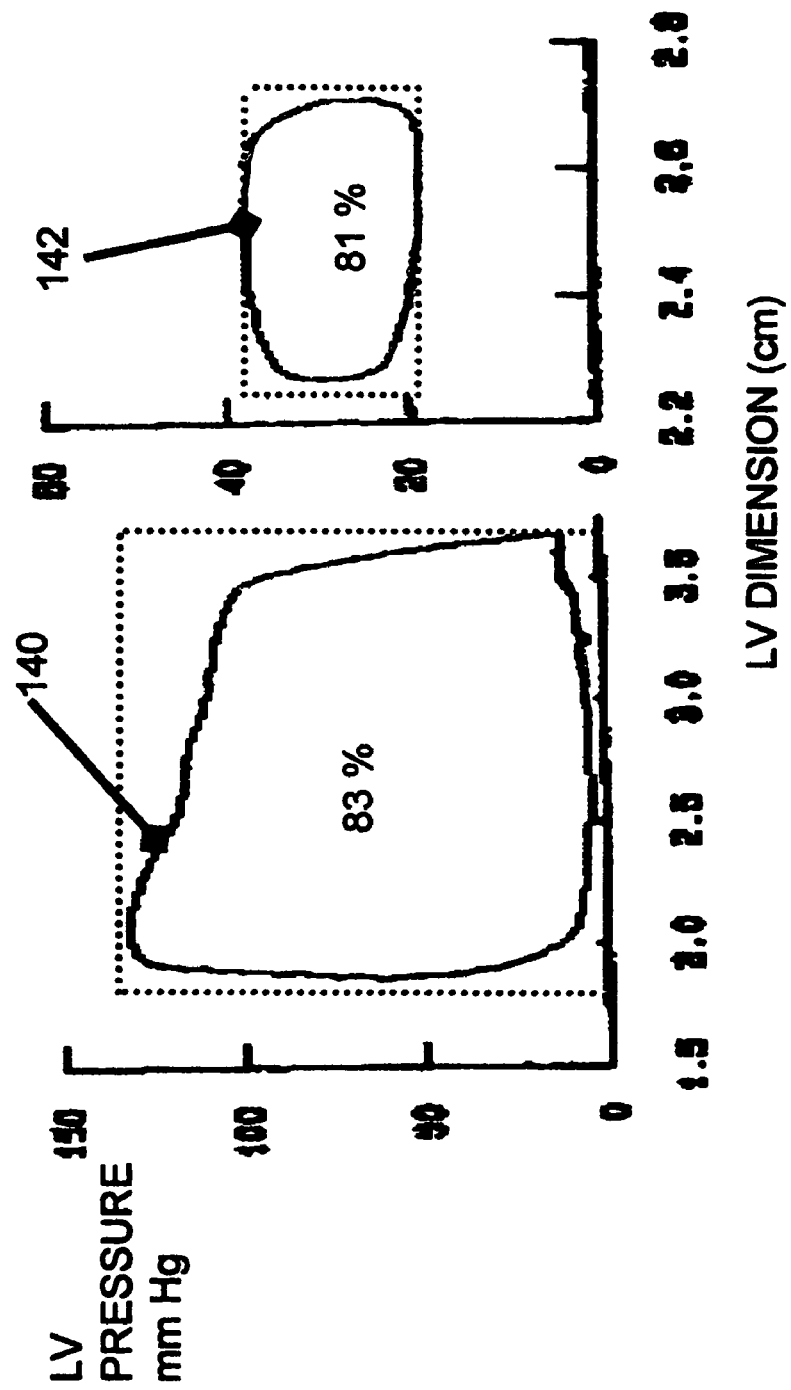

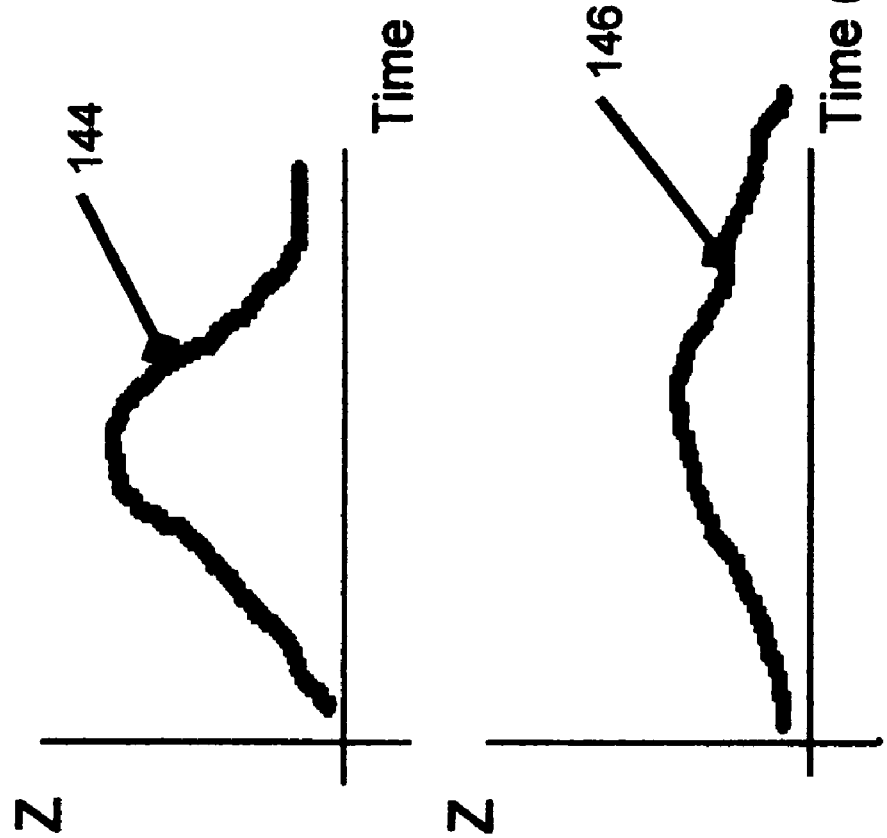

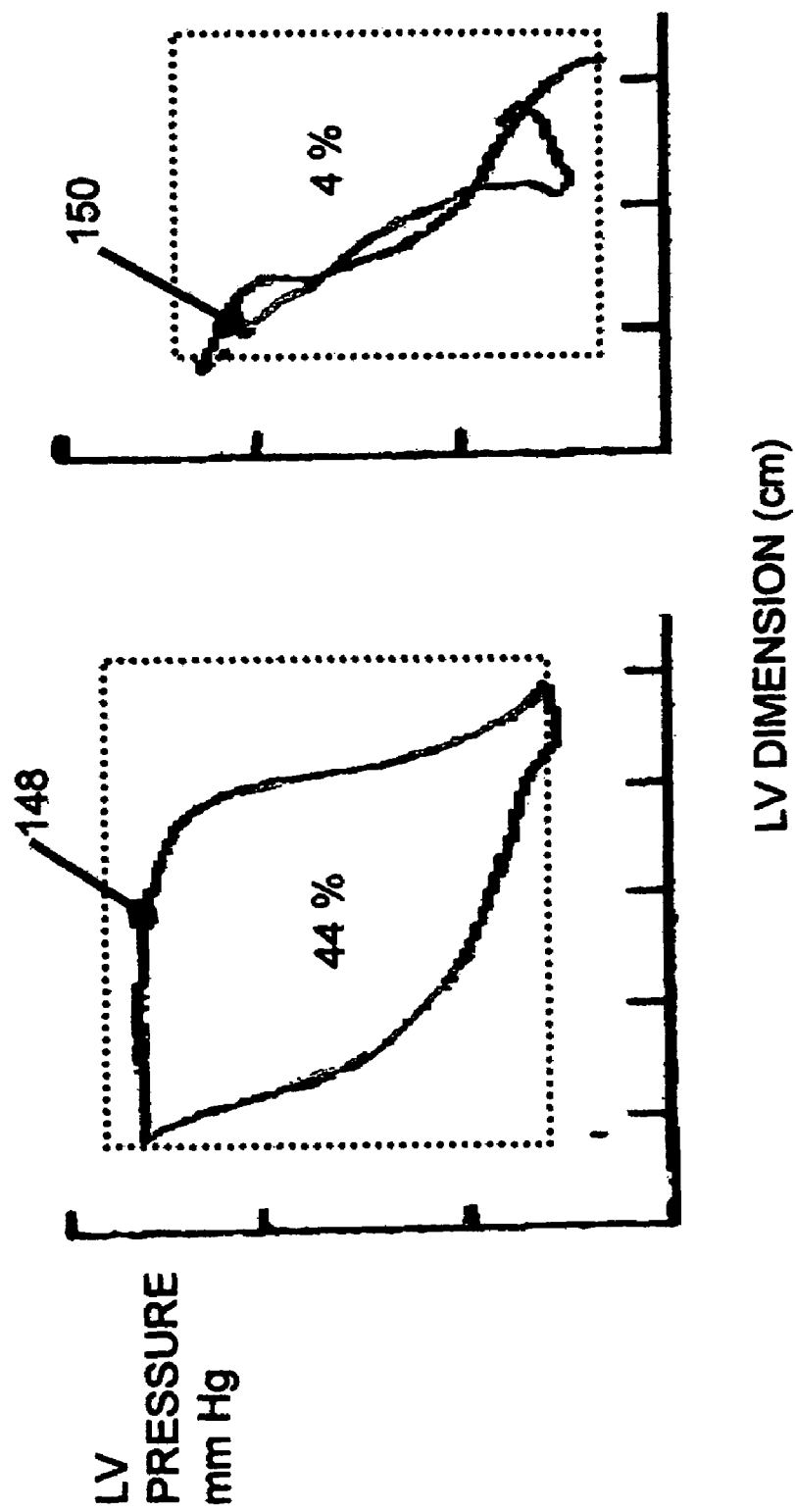

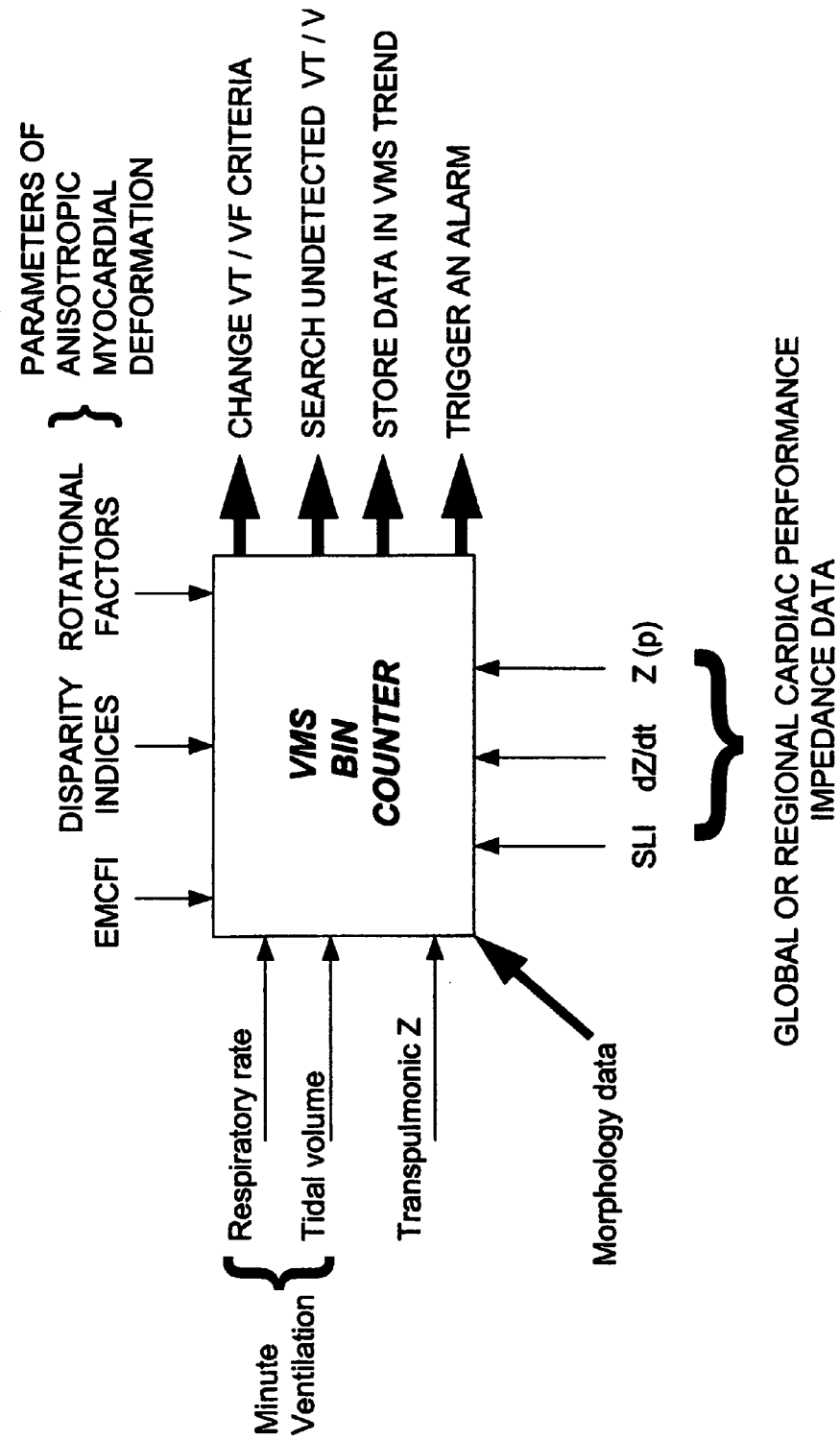
Figure 14: Vital Monitoring System

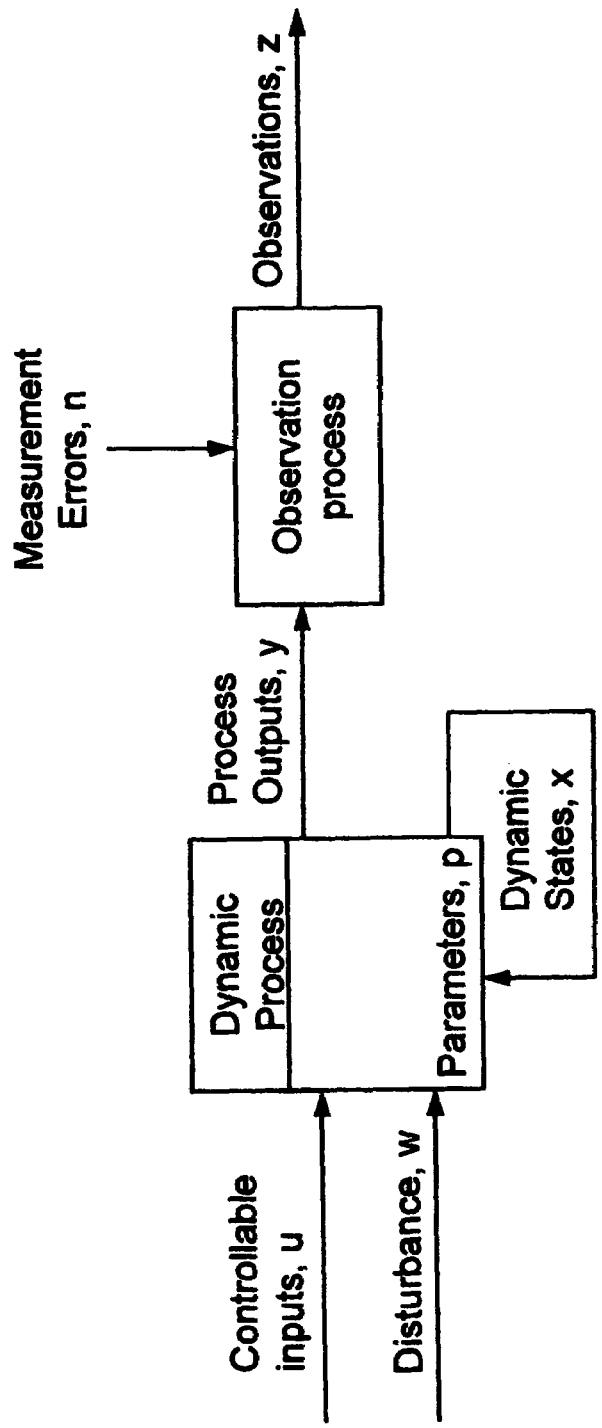

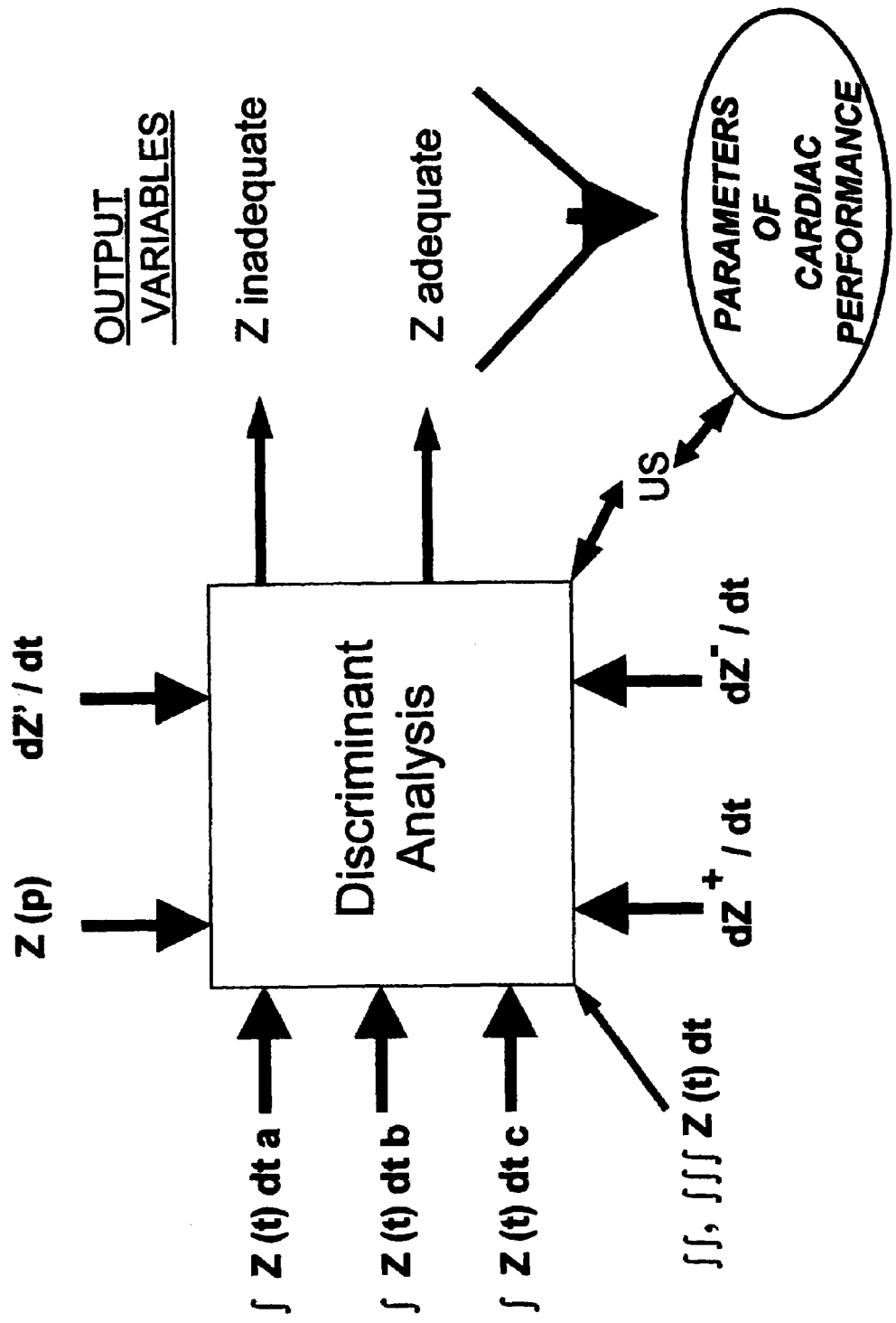

*Figure 20a*

1 - Determine if patient at rest with accelerometer
2 - Determine if patient at end expiration or hypopneic / apneic w/ minute ventilation sensor
3 - Acquire Z (t) dt and subtract static baseline Z value (offset), then store static thoracic impedance data in VMS to calculate parameter data / use in automatic optimization algorithms and store trend data (e.g. TPI)
4 – Repeat steps 1 – 3 over C cardiac cycles for ensemble averaging of Z (t) dt; use Runge-Kutta integration for data sampling
5 – Determine signal adequacy ( comparison to previously acquired template using echo interface at initial data entry, comparison to template data from historical controls stored in data bank, morphologic statistical comparisons using partial differential equations, assessments of signal continuity, using Discriminant analysis (etc)
6a – Derive Global or Regional Cardiac Performance data from waveforms (SCP, LCP,SLI, GCRP, dZ/dt, dZ'/dt, Z(p), TPI etc) and store in VMS, Vital Monitoring System, for trend data. Utilize Z in VTS, Vital Therapeutic System, for deriving CRT interval timing
6b – Utilize data in 6a for VTS as to optimize interval timing w/algorithms e.g. Matrix Optimization Method (MOM), measurements of cardiac performance, anisotropic myocardial deformation (AMD), blended parameters of GCP and AMD
7 & 8 – If signal is inadequate for GCP & AMD determinations use signals for calculating relative time to peak Z from EGM onset (if EGM R# = Z(p) #) to derive EMCFI (MOM)
9 – Can Z (t) dt in transvalvular or other vector(s) be used to extrapolate time of AoVc
10 – Use time of AoVc for derivation of time of post-systolic positive impedance (tPSPI), analyses of aortic valve function (VMS) and application in the VTS for interval timing
11 – Signal:noise ratio unfavorable, use stored interval timing from echo interface
12 – Use MOM, Matrix Optimization Method, with VrVI and other interval timing such as AV delay as to derive combination of interval timings that optimize measurement of cardiac performance (e.g. dZ/dt) and / or minimize AMD (anisotropic myocardial deformation), such as rotational factors, coronary sinus EGM disparity indices, multi-site CS peak Z disparity etc.
13 – Use Automatic Optimization Algorithm to confirm currently used parameter derived interval timing does not lead to clinical deterioration. The AOA algorithm will use measurements of GCP (e.g. GCRP, SLI) for highest signal fidelity conditions and use TPI, transpulmonic impedance index, in conditions of minimal signal integrity. Intermediate signal fidelity conditions will allow for use of dZ/dt, peak Z [Z( p)], obtained from multipolar electrode configurations of from summation averaging of regionally derived impedance signals deemed adequate with Discriminant Analysis
14 – CRT interval timing derived from ultrasound interface is implemented under conditions of inadequate signal fidelity and is evaluated with the AOA. Multiple stored interval timing states can be tried using trial and error and AOA evaluations.

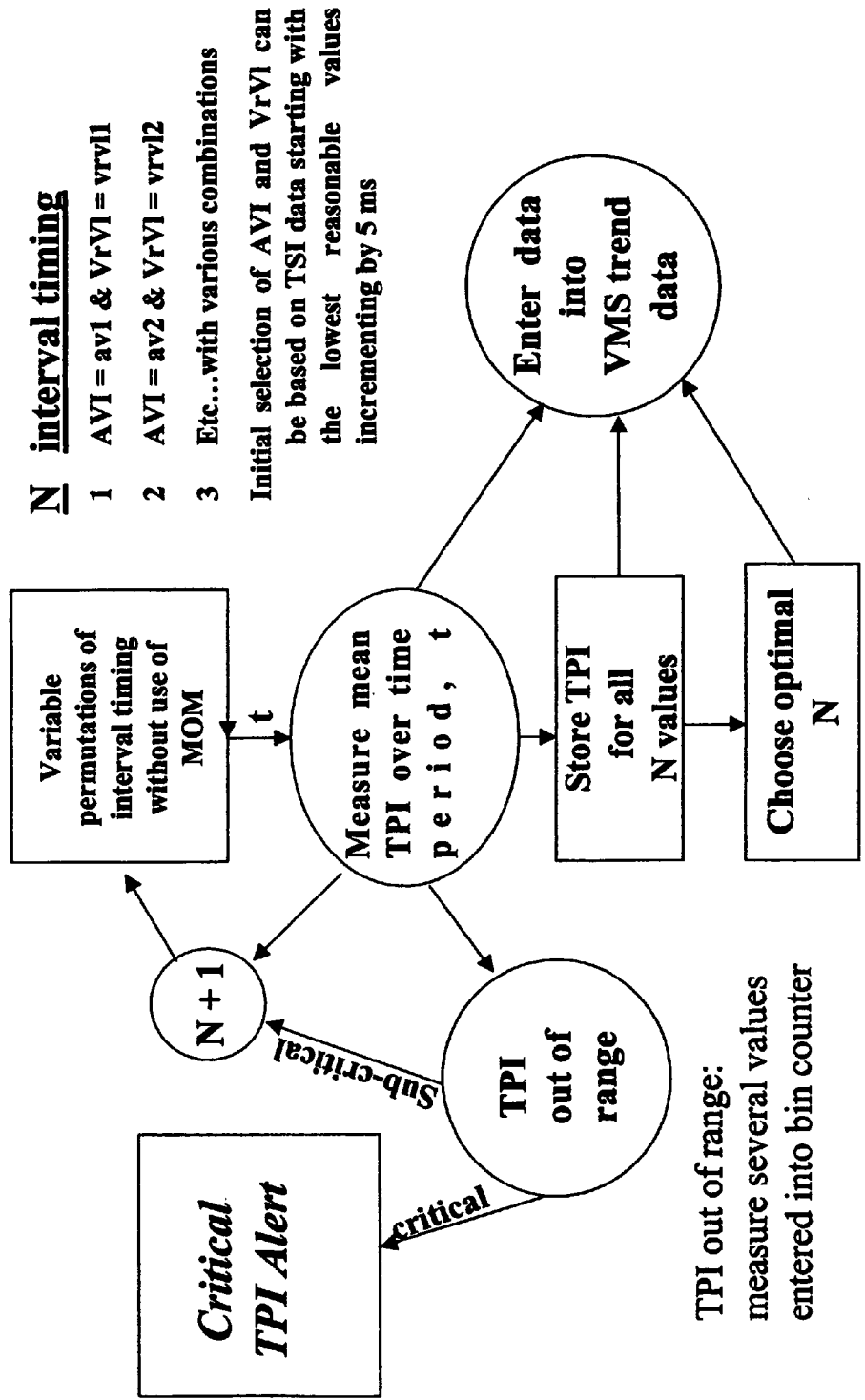

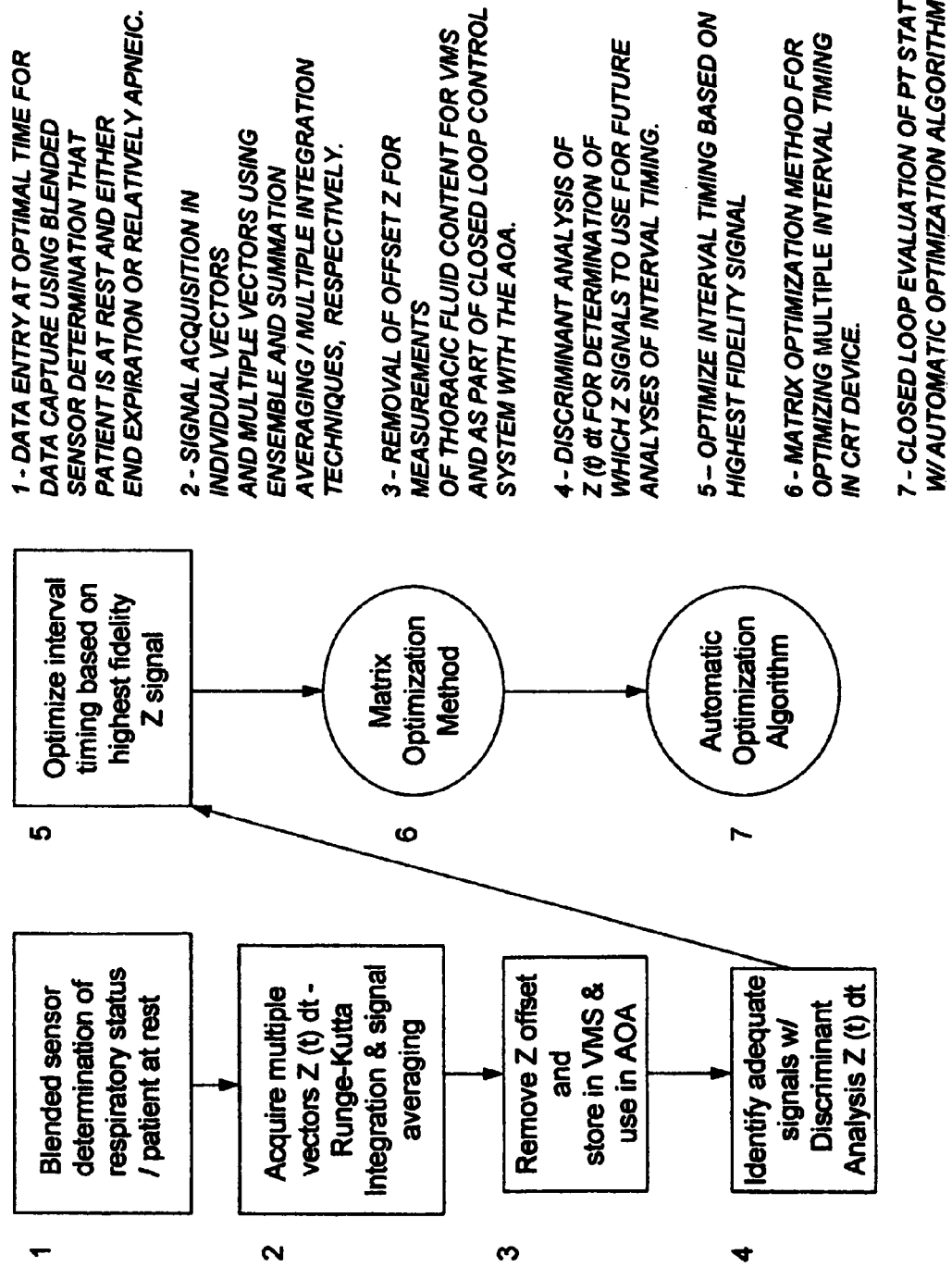

OPTIMIZATION OF IMPEDANCE SIGNALS FOR CLOSED LOOP PROGRAMMING OF CARDIAC RESYNCHRONIZATION THERAPY DEVICES

RELATED APPLICATIONS

This application is a continuation-in-part of application Ser. No. 10/779,162 filed Feb. 14, 2004, and incorporated herein by reference.

BACKGROUND OF THE INVENTION

1. Field of Invention

This invention pertains to an implantable CRT device that includes electrodes and means for dynamically measuring various impedance-related parameters and using these parameters for programming the CRT.

2. Description of the Prior Art

Current implantable cardiac resynchronization devices (CRT) are designed to improve congestive heart failure symptoms in cardiomyopathy patients with electromechanical dysynchrony. Most physicians implant CRTs without modification of the default programmed interval timing and as such a significant percentage of patients do not have improvements in heart failure symptoms. Current CRT essentially pace the RV and LV simultaneously. However, future CRTs will have a programmable delay between pacing in the RV and LV.

SUMMARY OF THE INVENTION

A substantial amount of data is available that demonstrates that small changes in interval timing between the RV and LV can reduce dysynchrony and improve congestive heart failure symptoms. As the status of an individuals heart can change acutely (congestive heart failure, myocardial ischemia/infarction) or chronically (remodeling) changes in interval timing may be needed over time. Ideally, CRTs can self adjust this interval timing as part of a closed loop system. Parameters based on extrinsic diagnostic evaluations such as ultrasound imaging or measurements of extrathoracic impedance to guide programming of CRT may be useful at periodic intervals but implementing such modalities can be time consuming. Use of an interface between CRT and extrinsic diagnostic systems will help accomplish CRT programming, but will not provide a dynamic means of control. Intracardiac electrograms and impedance measurements provide a window into intrinsic electromechanical events and are ideal for use in such a control system. Signal processing of impedance data over time has limitations. The methods and means of identifying which impedance signals are adequate for use as diagnostic data for monitoring purposes is described herein. Such diagnostic data is then optimized and implemented as to direct programming of interval timing in a closed loop control system.

BRIEF DESCRIPTION OF THE DRAWINGS

FIGS. 3, 3a, and 3b depict the rotation and translation of the left ventricle (LV) during the cardiac cycle using ultrasound techniques of Tissue Velocity Imaging. FIG. 3a illustrates how the regions sampled are relatively orthogonal to ultrasound beam. FIG. 3b illustrates the septal and lateral wall regions of interest.

FIG. 5 is a table describing varying degrees of impedance signal fidelity requirements.

FIGS. 13a–f in general shows how dysynchrony can exist in a pathologic heart at baseline or during ventricular tachycardia with both pressure-dimension loops and impedance waveform morphology. FIGS. 13a and b are pressure dimension loops in a patient without advanced structural heart disease in normal sinus rhythm and ventricular tachycardia, respectively. FIGS. 13c and d are impedance waveforms in the same patient under the same circumstances showing changes in the impedance waveform. FIGS. 13e and f are pressure dimension curves in a patient with cardiomyopathy in normal sinus rhythm and ventricular tachycardia. Such a patient will have more degradation in the impedance waveform than a patient with less advanced structural heart disease.

FIG. 14 illustrates how the Vital Monitoring System (VMS) uses a variety of data as to modify tachyarrhythmia therapies.

FIG. 15 is a representation of a stochastic optimal control system relevant to the technologies discussed in this patent application.

FIG. 16 illustrates how multivariate statistical analysis such as Discriminant analysis techniques assesses a varieity of impedance data/waveforms and determines which parameters are suitable representations of cardiac performance.

FIG. 20a outlines the steps in the dynamic control system.

FIG. 22a illustrates the functioning of the Automaic Optimization Algorithm (AOA) with parameters reflective of Global Cardiac Performance, GCP.

FIG. 22b illustrates the functioning of the Automatic Optimization Algorithm (AOA) with parameters descriptive of dysynchrony (and not cardiac performance) which are of less fidelity than those of GCP shown in FIG. 22a.

FIG. 22c illustrates how an AOA can use measurements of transpulmonic impedance to evaluate the efficacy for any given set of interval timing without need for higher fidelity data. Such an algorithm will not use the MOM, matrix optimization method, (motherless) as the signal to noise ratio is inadequte for any of the cardiac performance parameters or measurements of dysynchrony utilized in FIGS. 22a and b.

FIG. 27 summarizes how different control systems may inter-relate.

DETAILED DESCRIPTION OF THE INVENTION

Figure 1:
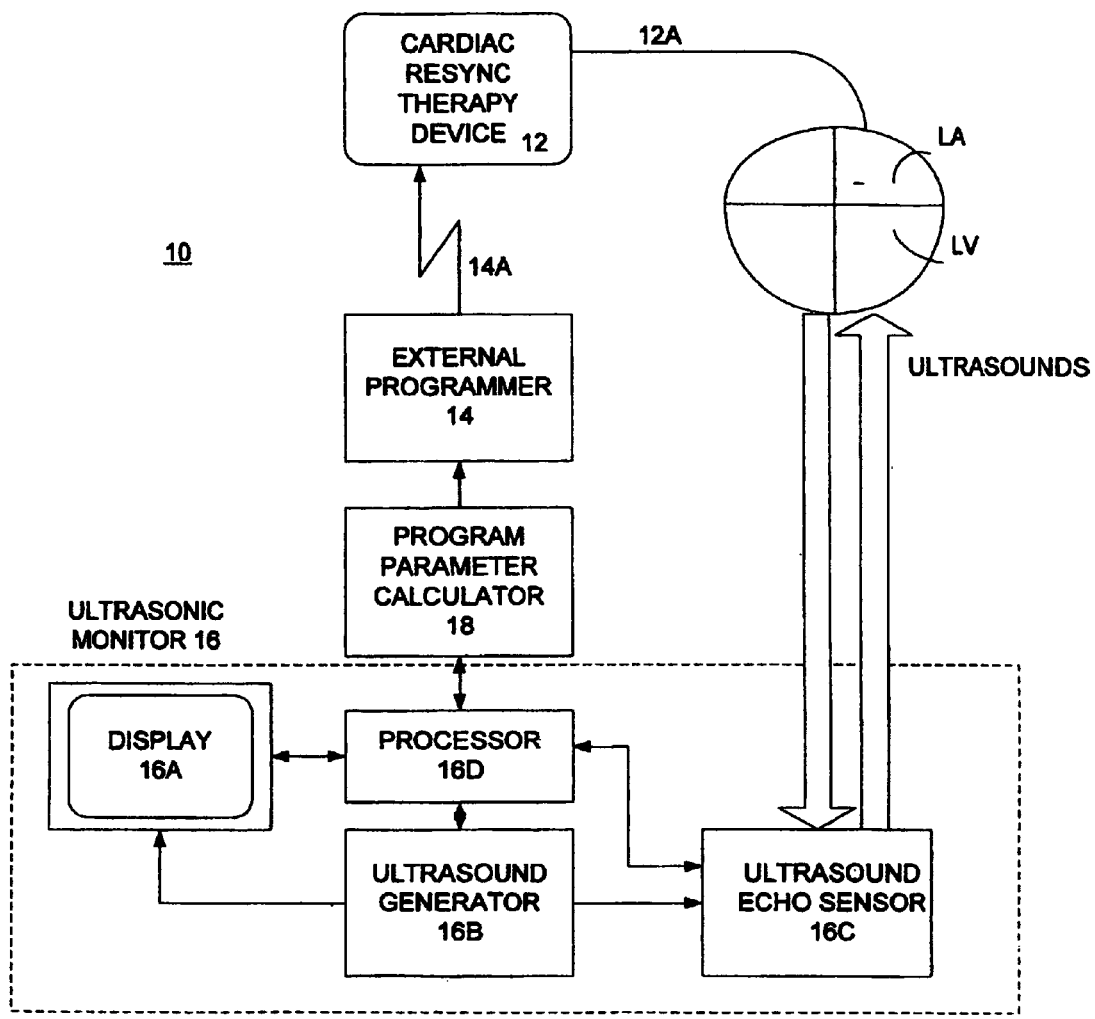
FIGS. 1 and 2 depict the apparatus and flow diagram for automatically programming a CRT device.

A method and apparatus for programming CRTs is disclosed in the parent application Ser. No. 10/779,162 (and are repeated here for convenience in FIGS. 1 and 2). FIG. 1 shows an apparatus for programming a cardiac device such as a CRT (cardiac resynchronization therapy) device 12. The device 12 includes a lead or leads 12A with several electrodes positioned to provide sensing and excitation in a patient's heart H, as discussed in more detail below, including sensing and pacing of at least the right atrium and right and left ventricles]. For the sake of simplicity, the electrodes have been omitted.

The apparatus 10 further includes a programmer 14 with a wand 14A. The wand 14A is used to transmit data from the programmer to the device 12. As part of this process, the device 12 receives commands to send stimulation signals to the respective cardiac chambers, and to sense the corresponding cardiac response, as discussed in more detail below.

The apparatus 10 further includes ultrasonic equipment 16. The ultrasonic equipment 16 includes a display 16A, an ultrasound generator 16B and an ultrasound echo sensor 16C. These elements are controlled by a processor 16D. Ultrasonic display 16A displays images derived from reflected ultrasound waves generated by the ultrasound generator, 16B, and received by ultrasound sensor, 16C, after processing in processor, 16D. The processor, 16D, receives the echoes and provides various information for a user such as a cardiologist or a clinician through the display 16A. The display 16A may include either a touch screen or other means (not shown) through which the user can provide input to the processor 16D. For example, the user may select portions of an image on the display 16D and request further information associated with the selected portions, request further data processing associated with the selected portions, or request some other data manipulations as discussed below.

The display 16A may show, directly, or indirectly, a live picture of the heart and its tissues, the operation of the valves and some parameters such as blood flow, myocardial thickness, myocardial velocity/strain, ejection fraction, cardiac dimensions, and so on. Ultrasound equipment of this type is available, for example, from GE, ACUSON and Philips.

Importantly, there is also provided a program parameter calculator 18 that operates in an automatic or semi-automatic mode to determine the programming parameters for the device 12. The calculator 18 is shown in FIG. 1 as a separate element, but it can be incorporated into the programmer 14, the ultrasound equipment 16 or even the device 12.

Figure 2:
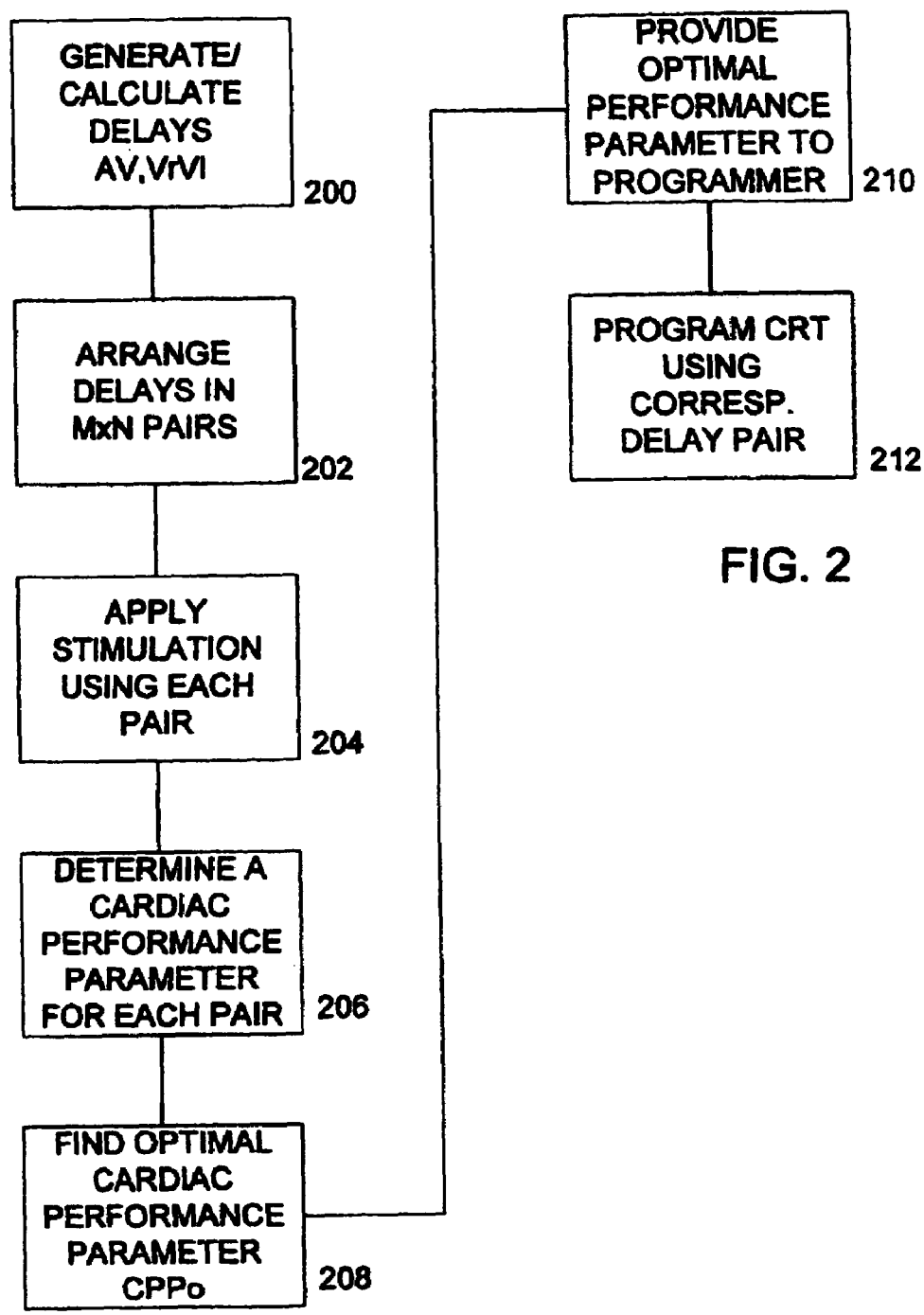

The general operation of the apparatus 10 is now explained in conjunction with the flow chart of FIG. 2. In step 200 one set of AV (atrial-ventricular interval) and VrVl, interval (programmed delay time between stimulation between electrodes in the right and left ventricles) and, optionally, other delays which may relate to intraventricular time delays, VaVb, (e.g. the delay time between stimuli delivered to a posteriorly positioned coronary sinus LV lead, Va, and laterally positioned coronary sinus LV lead, Vb) associated with the operation of the CRT 12 are selected. This can occur either automatically by the program calculator 18, or manually. Alternatively, these delays may be preprogrammed parameters. As described, the AV delays are between the right or left atrial and the right or left ventricular pulses, the VrVI delays are between the left and the right ventricular pulses and VaVb are between other electrodes (e.g. multi-site coronary sinus left ventricular electrodes). For example, five AV delays may be selected at 90±20 msec in 10 msec intervals (e.g., 70, 80, 90, 100, 110) and five VrVI delays may be selected at 0±20 msec in 10 msec intervals. Of course, any number M AV delays may be used and N VIVr delays may be used. The one set of delays form M×N delays times. These delays may be arranged into a two dimensional array or matrix for computational purposes (step 202). If three (or more) delay times (e.g. multiple interval timing, AV, VrVI, VaVb) are programmed then a multi-dimensional matrix can be used for computational purposes and M×N×P delay times will be analyzed. This will be referred to as the Matrix Optimization Method (MOM). Importantly, the AV can be predetermined using commonly employed equations (e.g. Ritter method) and not act as a variable for this matrix. With the predetermined AV delay programmed, only variables VrVI and VaVb need be evaluated using a two rather than a three dimensional matrix. This will reduce the number of delay times evaluated by this methodology. If two atrial leads are employed, RA and LA, the AV can reflect the time interval between the last stimulated atrial chamber (e.g. LA) and first stimulated ventricular chamber (e.g. RV) and be preprogrammed. The matrix optimization method described above can then apply to interval timing between the RA and LA and VrVl. As is readily apparent a number of permutations are possible which depend on the lead/electrode configurations implanted within a particular patient.

Next, in step 204 the CRT device is operated by the programmer 12 to stimulate the heart H sequentially using the set of delays defined in step 200. For example, the stimulation may be applied first using pulses with an AV delay of 70 msec and a VrVI delay of –20 msec.

In step 206, a predetermined cardiac performance parameter CPP is chosen. This parameter is indicative of the performance of the heart H responsive to these delays. This parameter can be derived from the ultrasonic monitor or ideally from within the CRT device itself. The inventor has described a number of parameters that are obtained from within the CRT device which are used for monitoring purposes and used to direct programming of interval timing in a closed loop control system. These performance parameters are collected automatically and provided to the program parameter calculator.

In step 208, the program parameter calculator identifies a cardiac performance parameter, CPPO, that is indicative of optimal cardiac performance (or, at least, the parameter that comes closest to indicating optimal performance).

In step 210, the pair of delays AVx, VIVrx corresponding to the optimal cardiac performance parameter is provided to the programmer 12.

In step 212 the programmer 12 programs these delays into the CRT.

The present inventor has discovered that impedance waveforms and impedance data derived there from are useful in directing the programming of the CRT. These waveforms can be used to describe a number of cardiac properties, including properties of dysynchrony and cardiac performance. The system automatically chooses the waveforms which have the most optimal signal to noise ratio (highest fidelity) and yield the most clinically relevant information. Utilization of such impedance data occurs autonomously though initial activation and periodic evaluations in conjunction with an ultrasound interface on an as needed basis may be performed at regular intervals.

Impedance Data Acquisition

Derivation of impedance waveforms using implanted lead systems is well known in the art and has been described in the literature. Data acquisition can be accomplished, for example, by delivering pulses of 200 uA, 30 us pulse width at a frequency of 128 Hz applied to two electrodes positioned along one vector (electrode pairs) and measuring the resulting voltage between electrodes located along the same vector. These pulses will not depolarize myocardium, cause only limited battery drain and have a frequency with an acceptable signal to noise ratio. The resultant time dependant impedance, $Z(t)$ peaks when there is maximal systolic ventricular wall thickness and minimal intracardiac blood volume.

The time dependent impedance signals or waveforms derived in this fashion relate to intrinsic myocardial properties. If signals are acquired between specific electrode pairs, the regional myocardial properties can be derived. The integrity of these waveforms may be subject to significant noise (poor signal to noise ratio) and inferior signal quality may result. This is especially true if data sampling occurs in a vector where there is impairment in myocardial contractile properties. Derivation of specific characteristics of these waveforms may suffice, even though overall signal quality is poor. Measurement of peak impedance and first and second order derivatives of impedance waveforms will relate to myocardial contractility. Assessment of the time required for a waveform to reach peak impedance will relate to myocardial synchrony if comparisons can be made to waveforms derived in alternate regions (e.g. right and left ventricular vectors).

Morphologic characterization of waveforms derived along multiple vectors is related to native myocardial contractile and relaxation properties (herein referred to as Global Cardiac Performance) and requires better signal fidelity than measurements of time to peak impedance or peak impedance. A comparison to normal waveform templates or changes in waveform morphology in a given patient reflects inter- and intra-individual variations in myocardial contractile (systolic) and relaxation (diastolic) properties.

Periodic Interval Monitoring—Analysis Activation

Periodic Interval Monitoring (PIM) at programmed intervals (e.g. every hour) occurs within the CRT. PIM serves to activate analysis of impedance and electrogram data if optimal conditions for such analysis exist. Optimal conditions include the patient being at rest (unless impedance signals during exercise have been previously determined to be adequate), and during periods of relative hypopnea/apnea. Use of a blended sensor such as an accelerometer and minute ventilation sensor can be used to define end-expiration or if possible a period of hypopnea/apnea where band pass filters can most easily eliminate impedance signal data related to changes in thoracic volume and cardiac translation within the thorax.

Impedance data acquisition can occur during intrinsic rhythm or during active pacing. Recently developed pacemakers utilize impedance data during pacing as to define the inotropic state of the heart. These pacing systems (Biotronik—closed loop system) adjust rate responsiveness based on a derived inotropic index, and are well known in the art. Defining intrinsic electromechanical properties (dysynchrony) initially will serve to direct the system to appropriately pace myocardium and cause resynchronization. This will need to be analyzed thereafter at periodic intervals during pacing as to confirm that adequate resynchronization is occurring. This can occur during pacing using electrodes that describe global cardiac properties or electrodes which have vectors that are similar to the electrodes used for stimulation. Techniques may be used to implement the same electrodes that are used for stimulation for data acquisition of impedance waveforms as well. Alternatively, and additionally, pacing may be terminated for reassessment of pathologic electromechanical properties with repeat adjustment of interval timing at periodic intervals.

Cardiac Translation

Cardiac translation occurs intermittently as a result of respirations and with cyclical periodicity during the cardiac cycle. This can cause degradation of impedance signals. Signal acquisition interruption (or integration time step halving; see below) and interpolation will reduce the affect of cyclical disturbances and improve the final signal to noise ratio. Though raw data may be lost during these intervals, specific assumptions about waveform morphology can be made using principles of continuity and estimations based on the probability density function of such scalar random sequences. Insight into timing of cardiac translation can be made using echo interface at time of initial data entry and at periodic intervals thereafter.

Figure 3A:
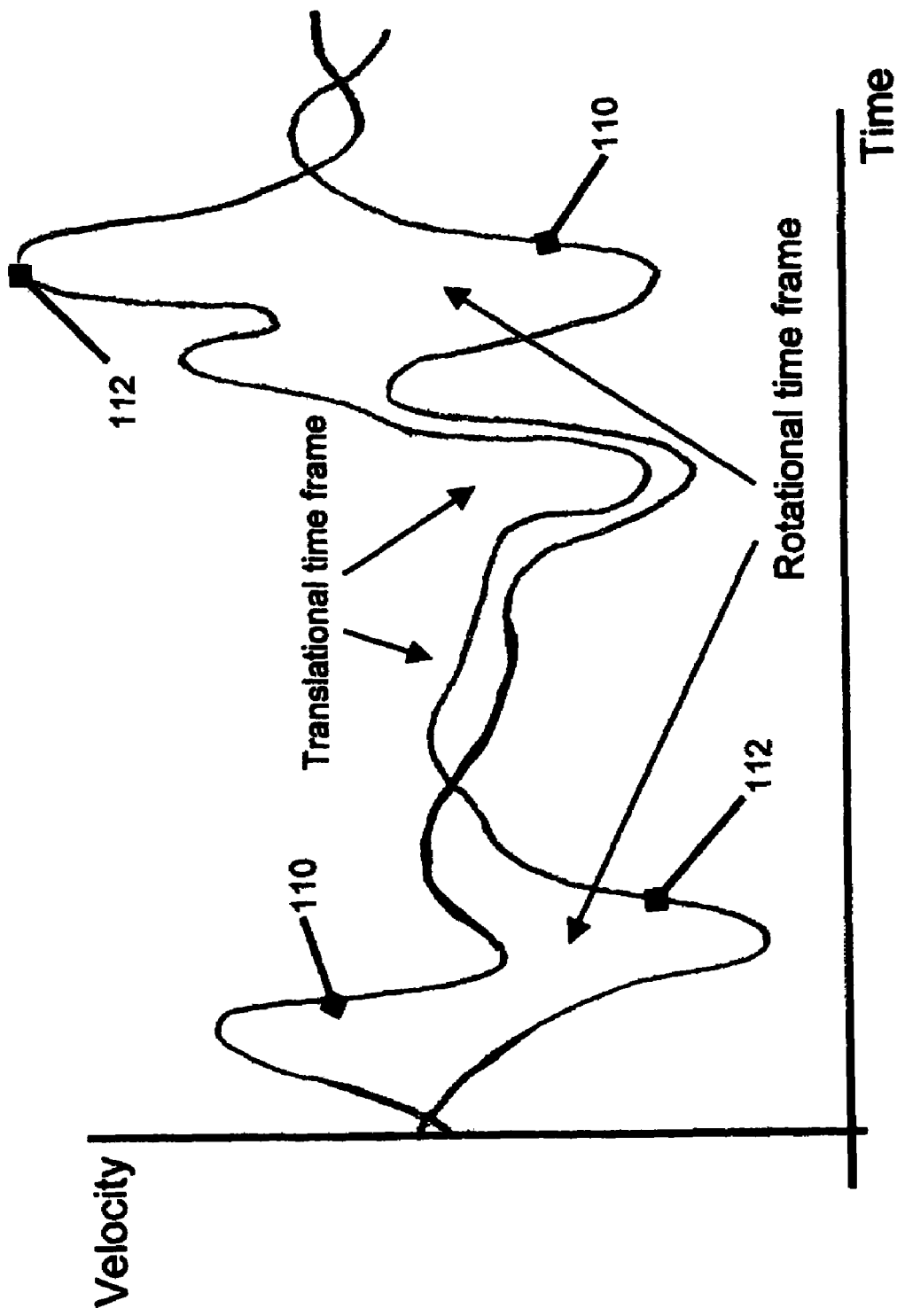
Figure 3B:
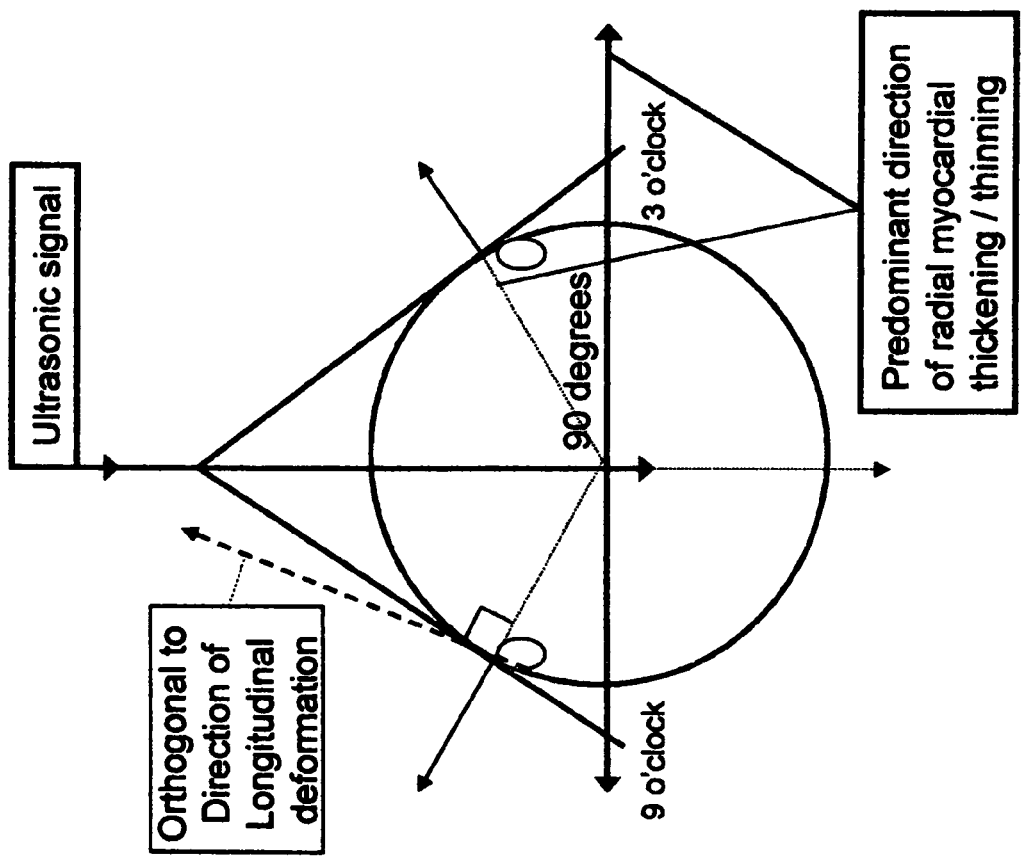

Parasternal short axis views with samples obtained in regions of interest where myocardial deformation is minimal (orthogonal to angle of insonification) will define translational time frames (FIG. 3). Signal interpolation can occur during these time frames, which can thus be defined on an individual basis using echo interface at time of initial activation/data entry. As to effectively define translation and not rotation or circumferential myocardial deformation the echo equipment should implement Doppler techniques of Tissue Velocity Imaging (General Electric) and eliminate regional strain effects by subtracting the spatial gradient of velocity within the region sampled (abstract submitted AHA 2004). Currently available equipment can not do this autonomously but has the capability if appropriate modifications to existing software were to be made. Importantly, the effects of cardiac translation will be reduced if one uses electrodes with vectors that traverse myocardium and not extra-thoracic structures.

Effect of Extra-cardiac Structures

Figure 4:
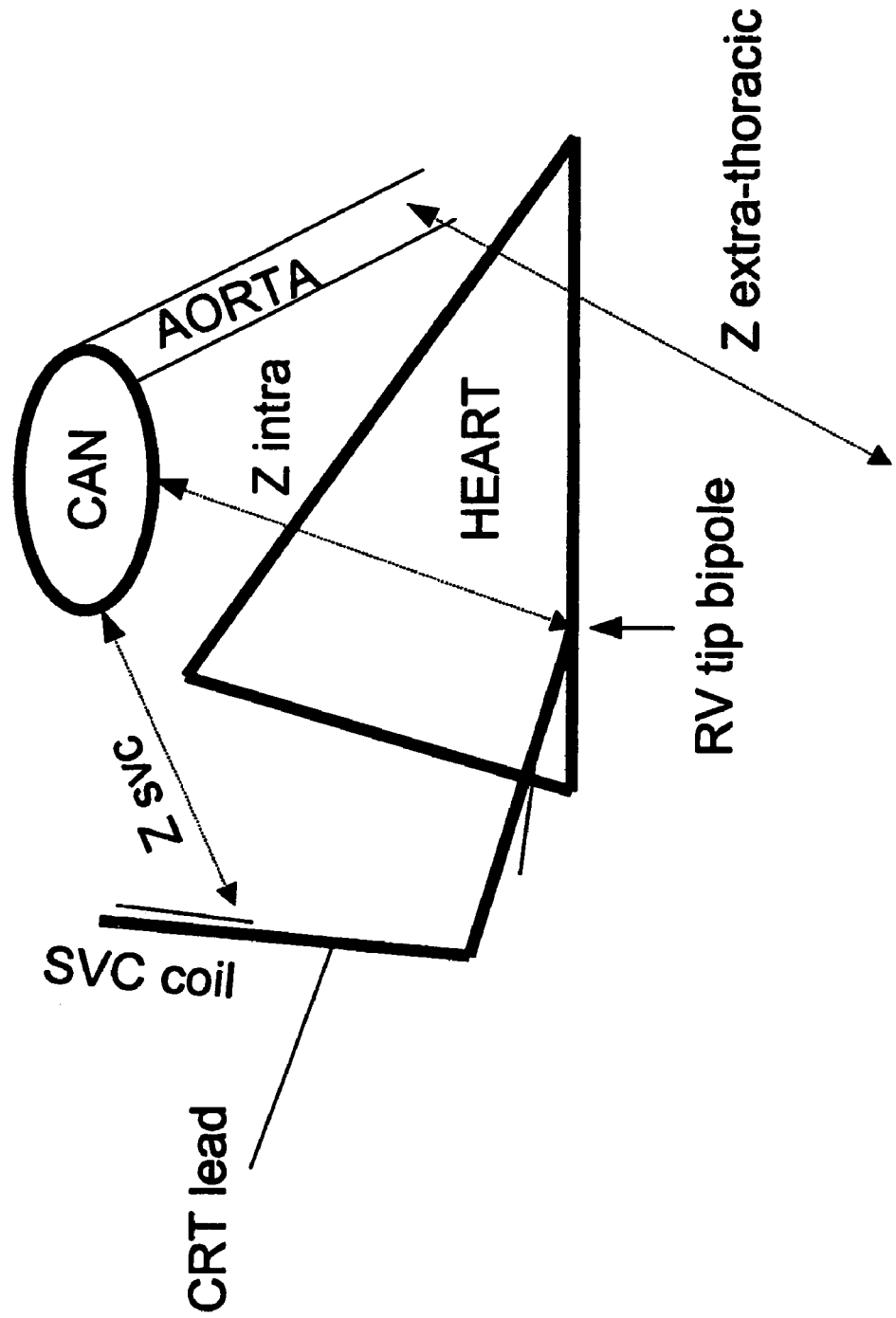
FIG. 4 illustrates the effects of extracardiac structures on impedance measurements.

Any electrode pairs or combination of electrode pairs may be used to gather impedance waveforms/data. Improvements in signal to noise ratio can be made by not using the device can as an electrode as this vector traverses significant lung parenchyma and the great vessels. Impedance changes related to the great vessels are indirectly proportional to intracardiac Z(t)dt as dZ/dt will be inverse. This is a result of systolic forward flow increasing aortic blood volume, which has a relatively low impedance value, compared to thickening myocardium. Normalizing Z(t)dt to impedance data obtained between the SVC coil and CRT can will help eliminate irrelevant signals related to the great vessels and respiratory variations if the can is used as an electrode. Alternatively, subtraction of Z(t)dt svc-can from intracardiac Z(t)dt will optimize the signal to noise ratio (FIG. 4).

Data Sampling and Integration Techniques

Techniques for integration of non-linear impedance waveforms generally rely on optimal waveform continuity and signal integrity. The robustness of the microprocessors and amount of battery longevity are considerations that must be accounted for as to minimize cost functions of such a control system. The Runge-Kutta integration technique is an example of how this can be performed. The larger the number of sampled increments obtained the better the signal quality will be. The disadvantage of using a greater numbers of increments is depletion of battery voltage, time for microprocessing and memory usage. Thus, data sampling should occur at periodic intervals and need not be continuous. In fact, the integration time steps need not be held constant and one can reduce computation during periods of "inactivity" (i.e. diastolic time frames) while retaining closely spaced computations during fast transients (i.e. systole or time of valvular events). As way of example, the magnitude of integration time steps can be doubled during systole and just after aortic valve closure and halved during the majority of diastole. This doubling/halving process is used for data sampling. As opposed to using one-step processes which involve only the last computed state plus a single increment, multi-step processes or predicator-corrector algorithms which utilize prior state computations will improve curve fitting by extrapolation if the costs to the system are not excessive.

Use of higher frequency current stimuli will cause current density to be more proximate to the electrodes being implemented and reduce far field noise. Variations in frequency, pulse width and current amplitude can be used as well in an effort to improve signal quality.

All data acquired can be used for monitoring purposes and assessment of optimal temporal relationships for pacing stimuli delivered by differing electrode pairs. In this fashion, intrinsic dysynchronous contractile properties can be mitigated and cardiac performance optimized.

Summation and Ensemble Averaging

Techniques of summation averaging and/or ensemble averaging over several cardiac cycles during periodic interval monitoring help optimize impedance data collection. Ensemble averaging will eliminate extraneous noise as the effects of random processes will be minimized for impedance waveforms derived between regional electrodes. This can be done by evaluating a number of cardiac cycles, C. Data acquisition will occur during periods of relative apnea and at rest. Blended sensor input from accelerometer and minute ventilation sensors will indicate which C are used for data capture. Analyses of Z(t) dt during periods of increased heart rate (e.g. exercise) can occur if signal to noise ratios are adequate. For the purposes of discussion herein we will discuss data acquired at rest though similar algorithms can be implemented during periods of exercise.

Summation averaging and techniques of integration of impedance waveform data gathered independently from regional electrodes can be used. Similarly, simultaneous multipolar data acquisition of impedance waveforms from multi-site electrodes can be used. Signals obtained in either fashion are then further processed with ensemble averaging techniques over C cardiac cycles.

Signal Fidelity Hierarchy

Impedance data can be derived in a number of different ways. Impedance waveforms which reflect the most clinically relevant information should always be used if possible. The inventor has described a number of different impedance parameters which reflect such cardiac properties. Such impedance waveforms will have the greatest requirements for signal processing and data analysis. If the fidelity of such acquired impedance waveforms is inadequate then the system will switch parameters and implement impedance data that requires less signal fidelity (FIG. 5). Such parameter switching occurs autonomously within the device or can be programmed as a default at the time of initial data entry or any other time frame. Parameter switching may cause the system to use lower fidelity data which only relates to dysynchrony rather than higher fidelity data reflective of both dysynchrony and cardiac performance.

Data descriptive of the morphologic characteristics of the impedance waveform itself require the highest fidelity signals. Descriptions of the impedance waveform curve (line integral) with equations or computation of the integral under the impedance waveform curve during specific time frames of the cardiac cycle will provide the most clinical information. This data describes systolic and diastolic properties as well as data related to electromechanical dysynchrony (see Global Cardiac Performance).

If such data can not be used as the signal to noise ratio is poor, the system will parameter switch and use alternate data such as the measured peak impedance (Z(p)), first or second order derivatives of the impedance waveforms (e.g. dZ/dt) or the relative time of peak impedance in different vectors (e.g. right and left ventricular leads). In order to yield the most clinically relevant information the system will need to define valvular events during the cardiac cycle.

Event Timing

Event timing relates to opening and closing of the heart valves. The most relevant event is closure of the aortic valve. Myocardial thickening that occurs after the aortic valve is closed is work inefficient and will lead to detrimental remodeling secondary to regional strain mismatch of normal contractile tissue and neighboring dysynchronous myocardial segments. Event timing can also relate to mitral valve opening and closing and aortic valve opening. If all events can be delineated we can define isovolumic relaxation, systolic ejection period and isovolumic contraction. This will allow us to temporally relate any signals monitored within the device to systolic and diastolic time frames throughout the cardiac cycle (temporal systole and diastole) to intracardiac electrogram signals. For descriptive purposes and by way of example, this invention will focus on aortic valve closure as this is the most relevant valvular event, which can be more readily defined with impedance waveforms. Impedance signals derived from intracardiac electrodes which best elucidate aortic valve closure will be utilized. By defining timing of such events, the appropriate correction factors may be applied to multi-site pacing stimuli. Implementation of such correction factors will allow intrinsically depolarized and extrinsically paced myocardium to contract synchronously during the systolic ejection period while the aortic valve is open (multidimensional fusion).

Event timing relates to times of myocardial contractility and relaxation, mechanical systole and diastole. Mechanical systole and diastole does not occur in all myocardium simultaneously. Delays in electrical activation (conduction abnormalities) and myocardial processes such as infarction (mechanical abnormalities) cause dysynchronous mechanical events. Such dysynchrony can be minimized, in part, by pre-excited stimulation of dysynchronous myocardial tissue at the appropriate time. This pre-excited interval (electromechanical correction factor, EMCF) can be derived through analyses of intrinsic electrograms and impedance signals.

Initial Data Entry

Once an implanted device and lead system has matured or fibrosed into a stable position, initial data entry should occur. This occurs approximately 3 months after implant of the CRT. At this point in time, template storage and quality assurance of intracardiac impedance data can occur. The CRT is programmed in an appropriate fashion after confirmation which acquired signals are adequate for activation of the true closed loop system using algorithms such as Discriminant Analysis (described below).

Use of an interface with echocardiographic equipment to identify valvular events and dysynchronous contractility patterns will be helpful for initial data entry. If signal processing is optimal, such an interface may not be necessary. Determinations of signal quality can be made using stored templates from data banks of patients with normal hearts, cardiomyopathy (CM) and eucontractile patients (reversible CM). At later time this can be done with comparisons of previously stored template data from the implanted patient. Confirmation of optimal signal quality will be described below. The methodology employed in application Ser. No. 10/779,162, details how to use of an interface with echo and extra-thoracic impedance measuring devices functions. Through this interface it can be confirmed that the intracardiac impedance signals correlate with valvular events and myocardial systole and diastole at time of data entry as well as at periodic intervals thereafter.

Defining Valvular Events—Nature of the Notch

Figure 6B:
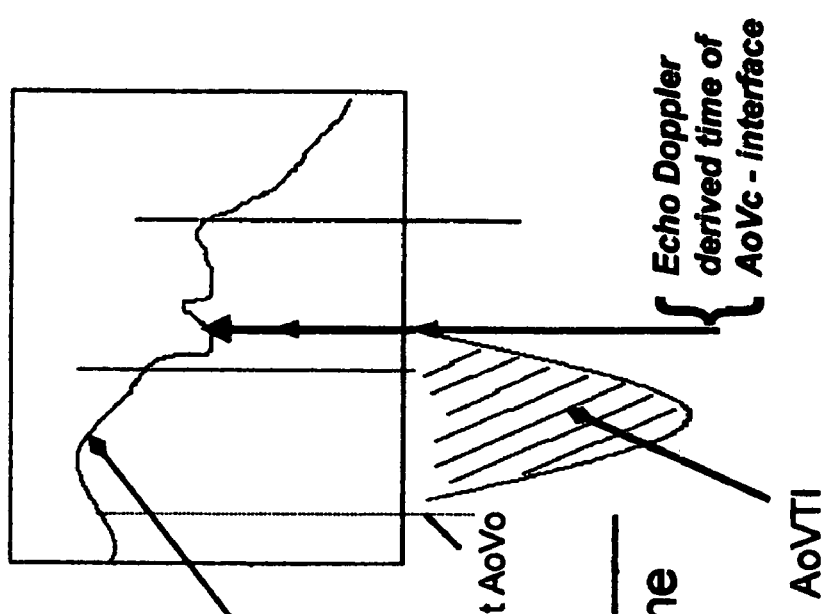
FIG. 6 demonstrates valvular event timing during the cardiac cycle and the relationship between the impedance signal and Doppler derived measurements of blood flow across the aortic valve as to accurately denote time of aortic valve closure.
Figure 6A:
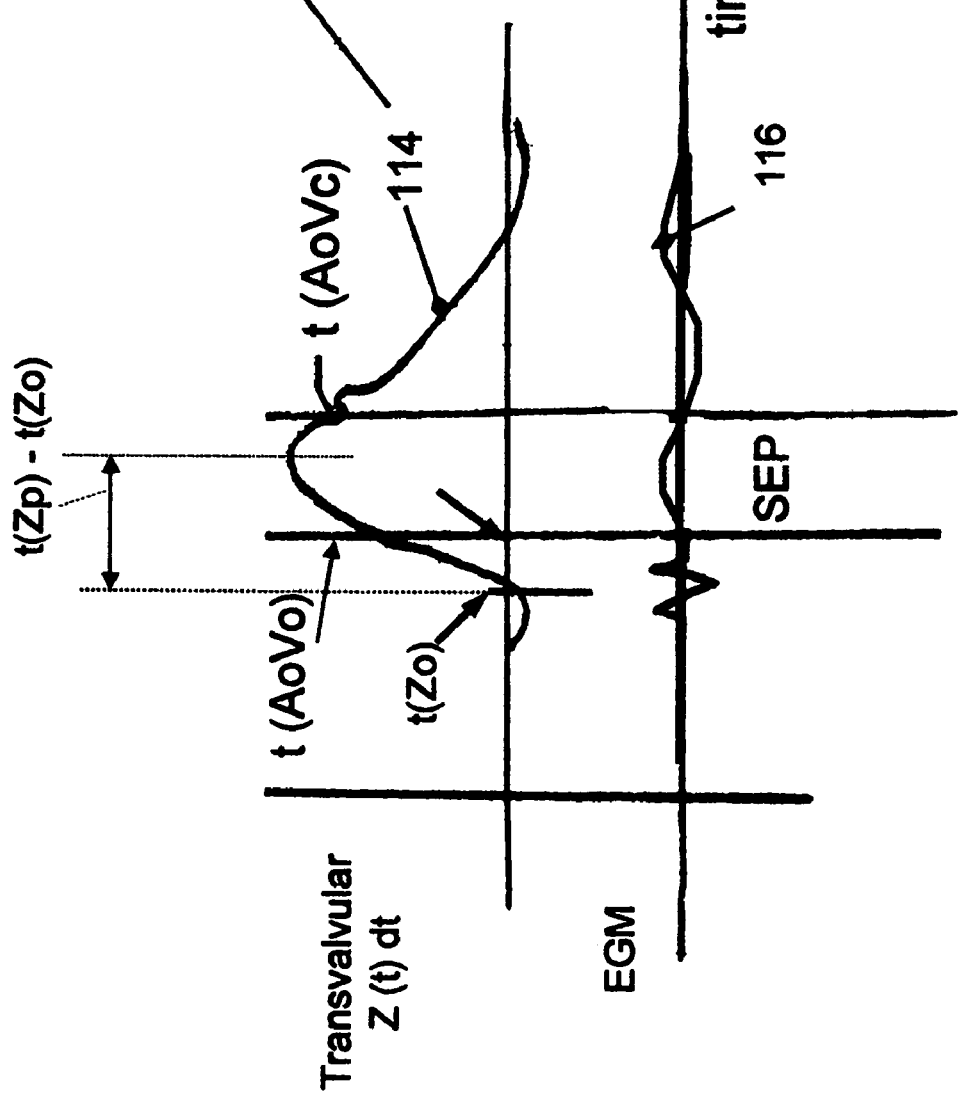
Figure 7:
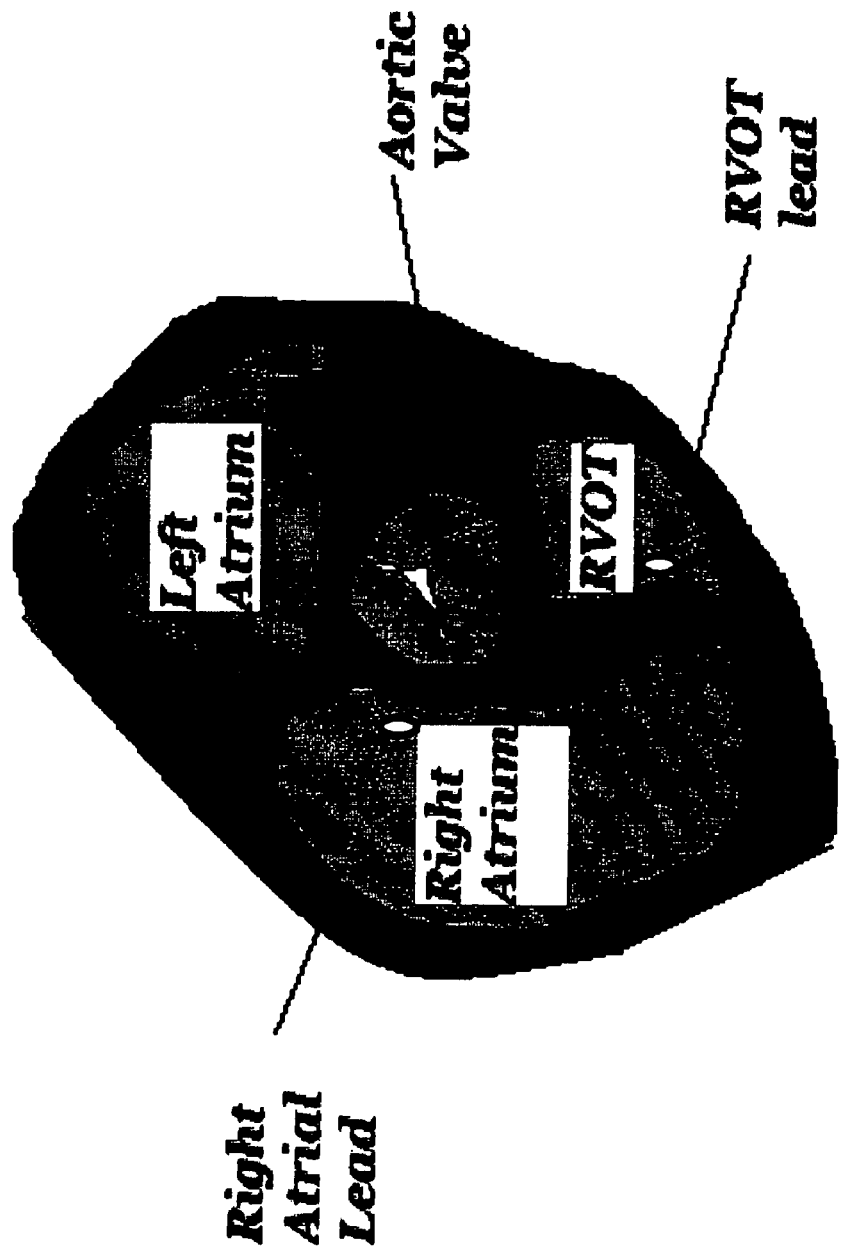
FIG. 7 illustrates cardiac chamber anatomy suitable for lead placement of electrodes that provide trans-valvular (aortic valve) impedance data.

Valvular events such as aortic valve closure can be defined by notching on the downward slope of the impedance signal (FIG. 6a). Such notching is apparent on signals derived from extra-thoracic impedance measuring devices as well. The nature of the notch can be descriptive of specific pathologic processes such as aortic stenosis/regurgitation and decreased cardiac output. These pathophysiologic states will cause changes in the time from upslope notching (aortic valve opening) and/or downslope notching to peak impedance (FIG. 6 and see below) and the morphology or nature of the notch itself (FIG. 6b). In one embodiment, analysis of this data can be used as part of the vital monitoring system detailing information about the aortic valve and not just timing of aortic valve events. Electrodes that traverse the aortic valve (right atrial appendage and right ventricular outflow tract) will be ideal for obtaining such impedance signals (FIG. 7). Global impedance data derived from multiple intracardiac electrodes can improve signal definition defining aortic valve events as well. Multiple integration techniques (via multi-polar electrodes) and use of summation averaging techniques for optimization purposes improve signal processing for such impedance data. The exact time in the impedance waveform (morphologic feature of the notch) that correlates with aortic valve events can be defined using the echo interface if impedance data alone does not accurately define this event (FIG. 6b) and such characteristics can be specified at time of initial data entry.

Characterization of aortic valve can be done with equations designed to assess timing of aortic valve opening and closure. Delays in the time between onset of positive dZ/dt (or EGM marker) to aortic valve opening will be seen in patients with aortic stenosis.

$$\text{Aortic Valve Function}=f(AoV)=[tAoVo-tZ(0)/dZ/dt]^{-1} \quad \text{Equation 1}$$

Where t AoVo=time of aortic valve opening; t Z(0)=onset time of positive impedance slope. The units are in ohm/sec$^2$.

The function includes dZ/dt to account for cardiac output though any measurement that describes cardiac performance can be substituted for dZ/dt (e.g. ∫ Z(t)dt). Low output states will cause a delay in time to aortic valve opening which will be a confounding variable and lead us to overestimate aortic valve stenosis severity. Comparisons over time in a given patient of Aortic Valve Function will lend insight into progression of aortic stenosis. Analyses of this function in large groups of patients with comparisons to other diagnostic evaluations of aortic stenosis will allow use of f(AoV) for estimation of valve area. This will require derivation of a correction factor based on such data. Similar equations can be made for assessment of aortic valve regurgitation using delays in time to aortic valve closure from either onset of aortic valve opening (systolic ejection phase) or from time of peak impedance, Z(p). Such analyses will require the most optimal signal fidelity.

Figure 8:
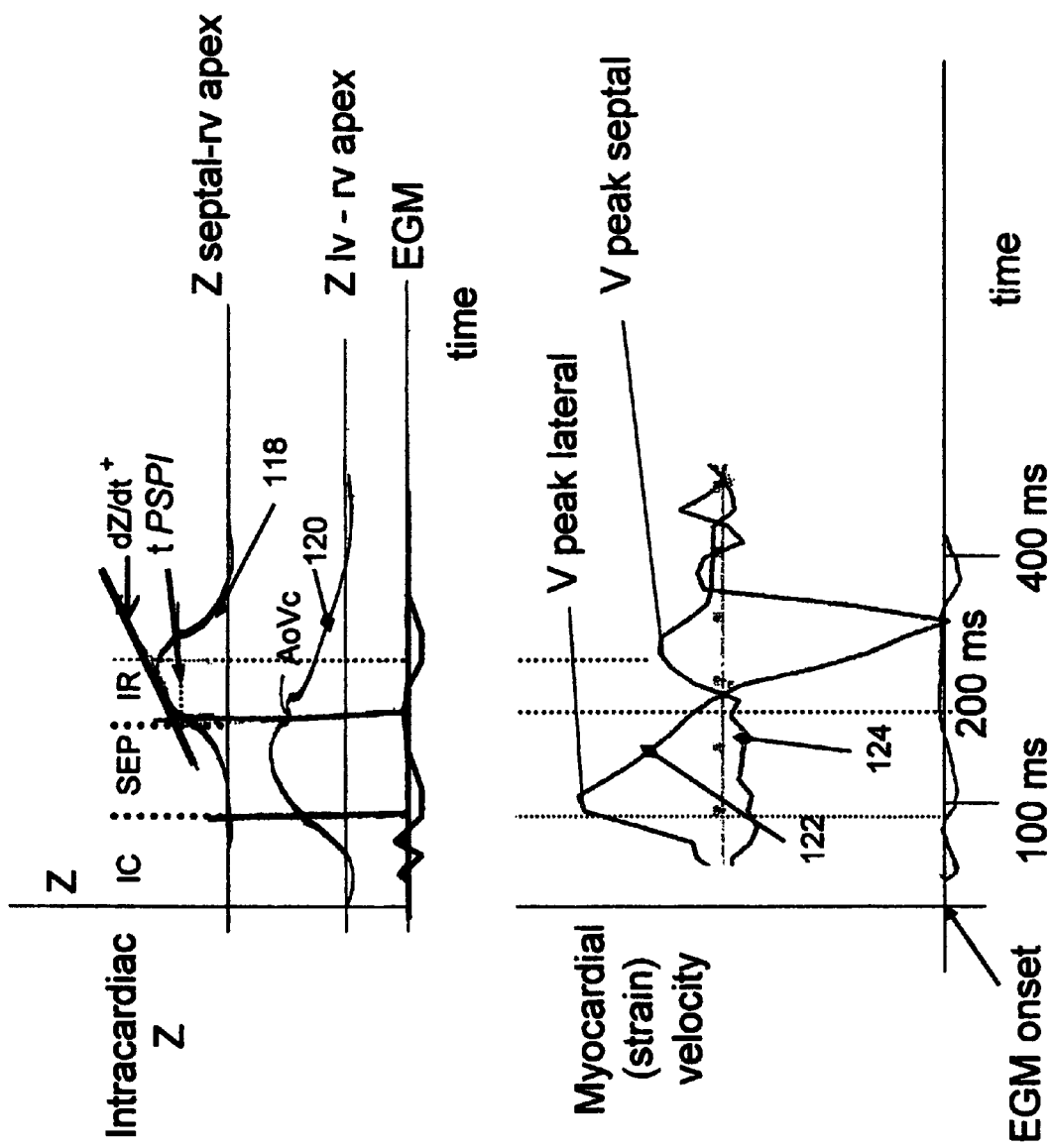
FIG. 8 depicts the relationship of impedance waveforms derived from right ventricular (RV) and LV vectors to myocardial strain (or velocity curves) representative of time to peak impedance and time of peak myocardial strain (or velocity), respectively.

Once valvular events can be identified using the impedance signal, this event can be extrapolated to any of the intracardiac electrograms signals for purposes of temporal correlation with other events such as myocardial thickening (FIGS. 6 and 8). Confirmation that a specific signal or summated signals appropriately identify valvular events can be periodically confirmed with an interface with echo. If signal fidelity is adequate this may not be necessary. Techniques such as doubling integration time steps (increased sampling frequency) during intervals where valvular events are historically expected to occur will help eliminate requirements for connectivity with other equipment.

Defining Myocardial Events

Mechanical myocardial systole and diastole can be identified by evaluation of impedance signals over time, Z(t) dt, as well. Z(t)dt across myocardial segments are characterized by peaks and valleys. Peaks represent peak myocardial thickening and minimal blood volume. Blood has a relatively low impedance value and maximally thickened myocardium will have peak impedance values. As Z(t)dt can be derived in specific myocardial segments between local electrodes, information about regional myocardial thickening is contained in this function. This information includes time of peak myocardial thickening and relative degrees of myocardial thickening. Such data can be used to identify changes in timing and degree of local contractility. As timing of contractility only requires identification of peak impedance for a specific segment or vector, optimal signal quality is not necessary. If signal processing optimizes a signal such that other data may be derived from the impedance signal such information can be used for the monitoring system and shed light on regional changes in myocardium (e.g. infarction). Confirmation that a specific signal or signals appropriately identify timing of regional myocardial thickening can be made through an interface with echo or within the device itself with Discriminant Analysis algorithms. Echo identification of time of peak myocardial velocity or time to peak myocardial deformation (strain measurement) will parallel time to peak regional myocardial impedance (FIG. 8). Time to onset of myocardial deformation, time of minimal regional intracavitary volume or other echo parameters descriptive of myocardial events can be used as well. These ultrasonic modalities are currently available using echocardiographic equipment manufactured by companies such as General Electric, Philips and Acuson. By this mechanism the CRT can be more accurately programmed to have time to peak impedance used as a parameter for the closed loop control system. Importantly, repeated assessment of timing of valvular events with intrinsic impedance data and via the interface may be necessary after changes in interval timing have been programmed, as timing of aortic valvular events may change (e.g. shorter systolic ejection period). Such an assessment can occur within the device if adequate impedance signal quality for defining valvular events is present.

Rate Responsiveness and Detection of Myocardial Ischemia

Changes in myocardial contractility patterns and conductivity vary with increased heart rate. Incremental delays in electromechanical events may occur in a pathologic fashion and as such, true optimization will account for this. Impedance signals during exercise often have inadequate signal to noise ratios. Increases in blood volume within the pulmonary vasculature that occur during exercise will affect the impedance signal and such offset impedance data is subtracted from the peaks and valleys in the impedance signal which reflects changes in myocardial thickness and intracavitary blood volume. Further degradation in impedance signals can be expected during exercise secondary to changes in respiration and increases in cardiac translation within the chest cavity. Formulation and programming of rate response curves in a fashion similar to AV delay optimization with increases in heart rate can be accomplished using an echo interface with pharmacological stress testing with an agent such as Dobutamine. Dobutamine will increase both the heart rate and the inotropic status of the heart without significant changes in patient movement and respirations. Evaluation of dyssynchrony with Dobutamine provocation and optimization of interval timing using the echo interface will allow for programming dynamic changes in interval timing resulting in more physiologic, dynamic control.

One will detect myocardial segments that are ischemic and find more significant delays in time to peak myocardial velocity and/or decreases in regional deformation in patients with compromised coronary vasculature. Similar data could be detected by analysis of regional delays in time to peak impedance and regional decreases in peak impedance values at higher heart rates. This would be contingent on adequate signal quality and in one embodiment could be used for the vital monitoring system. An exercise (non-pharmacological) stress echo can be performed while the echo interface is active and confirmation of adequate impedance signal quality with exercise can occur. In this fashion rate responsive changes in interval timing will not need to be empirically programmed but can be part of the closed loop control system and based on intracardiac impedance data alone. Use of a bipolar or multipolar LV lead would optimize signal quality for this type of dynamic analysis and reduce the affect of extraneous data (cardiac translation and variations in impedance from respiration). This is because more regional information can be derived between local electrode pairs positioned in myocardial tissue that is dysynchronous and extraneous data will not be accounted for.

Figure 9:
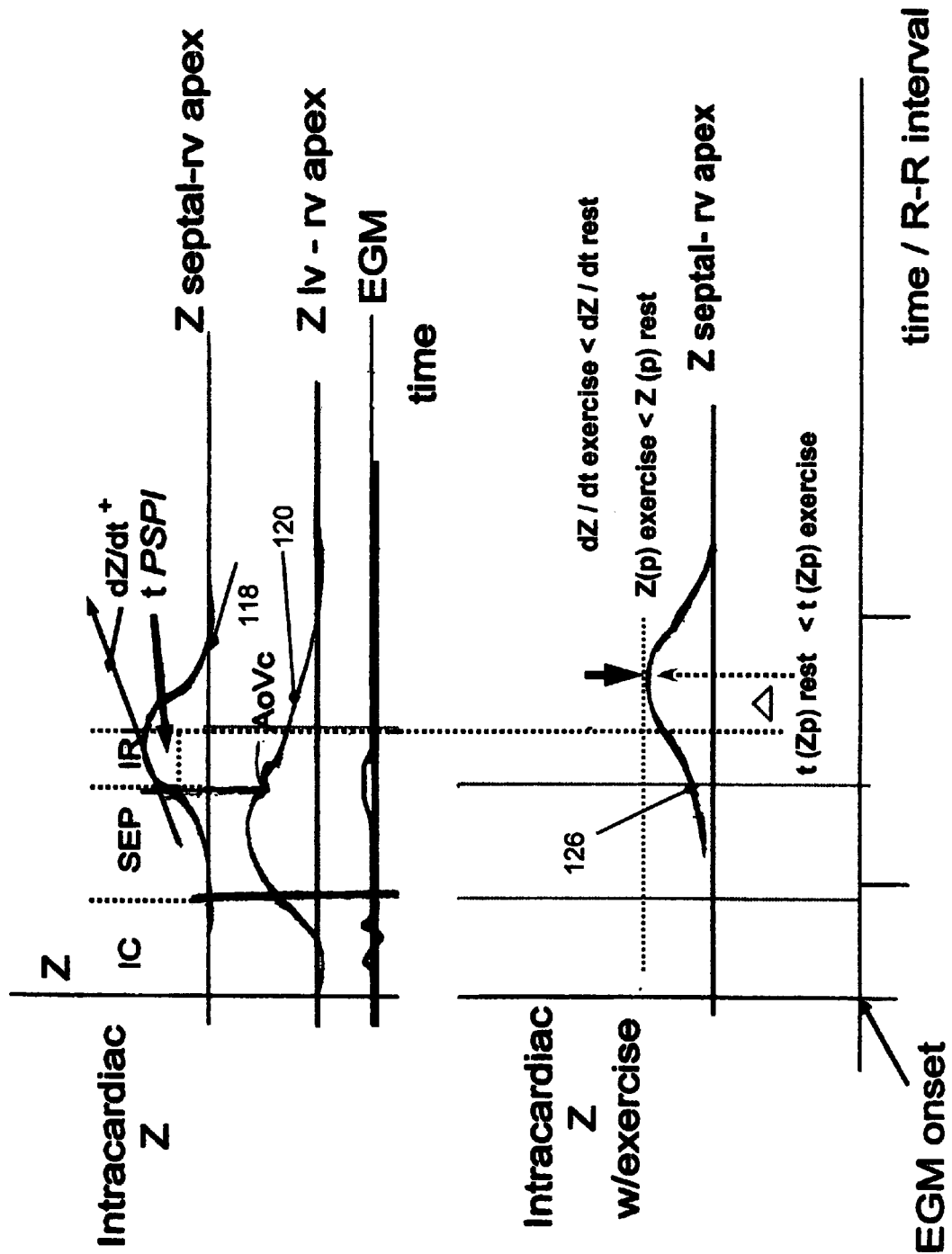
FIG. 9 shows changes in impedance waveforms with myocardial ischemia.

In one embodiment, delays in time to peak impedance and changes in the impedance waveform (e.g. time to onset of positive dZ/dt, time to peak Z, time to peak dZ/dt) and/or reductions in the quantity of the integral of Z or changes in the morphology of Z(t)dt, can serve to trigger a system alert and notify the physician that impairments in coronary reserve (ischemia or myocardial injury) are present (FIG. 9). In a preferred embodiment, reductions in rate responsiveness (decreases in slope of rate response and peak sensor rate) will occur as to limit myocardial ischemia when ischemic changes in impedance waveforms are detected.

Offset Impedance Removal

Impedance data that is not directly related to systolic and diastolic properties during the cardiac cycle is removed and used for additional analyses. Removal of the baseline offset impedance signal that relates to such "static" cardio-thoracic resistivity is necessary. This data relates in large part to structures within the thorax as well as dynamic changes in thoracic fluid volume. Though these changes are less dynamic compared to impedance variations related to the cardiac cycle, this data can still be used for monitoring purposes (thoracic fluid volume) and is incorporated into the control system as a means of checking that the current algorithm for optimizing interval timing is not causing clinical deterioration (see below—Automatic Optimization Algorithm). Subtraction of offset impedance may occur before derivation of impedance parameters or after analysis of signal vector adequacy or other time frame during signal processing if costs to the system are lessened.

The newly derived baseline impedance value and impedance waveform, Z(t)dt (line integral), will define the limits of integration in the Y axis, while specific times during the cardiac cycle (e.g. aortic valve opening and closing) will define the integral limits along the abscissa.

Global Cardiac Performance

Figure 12:
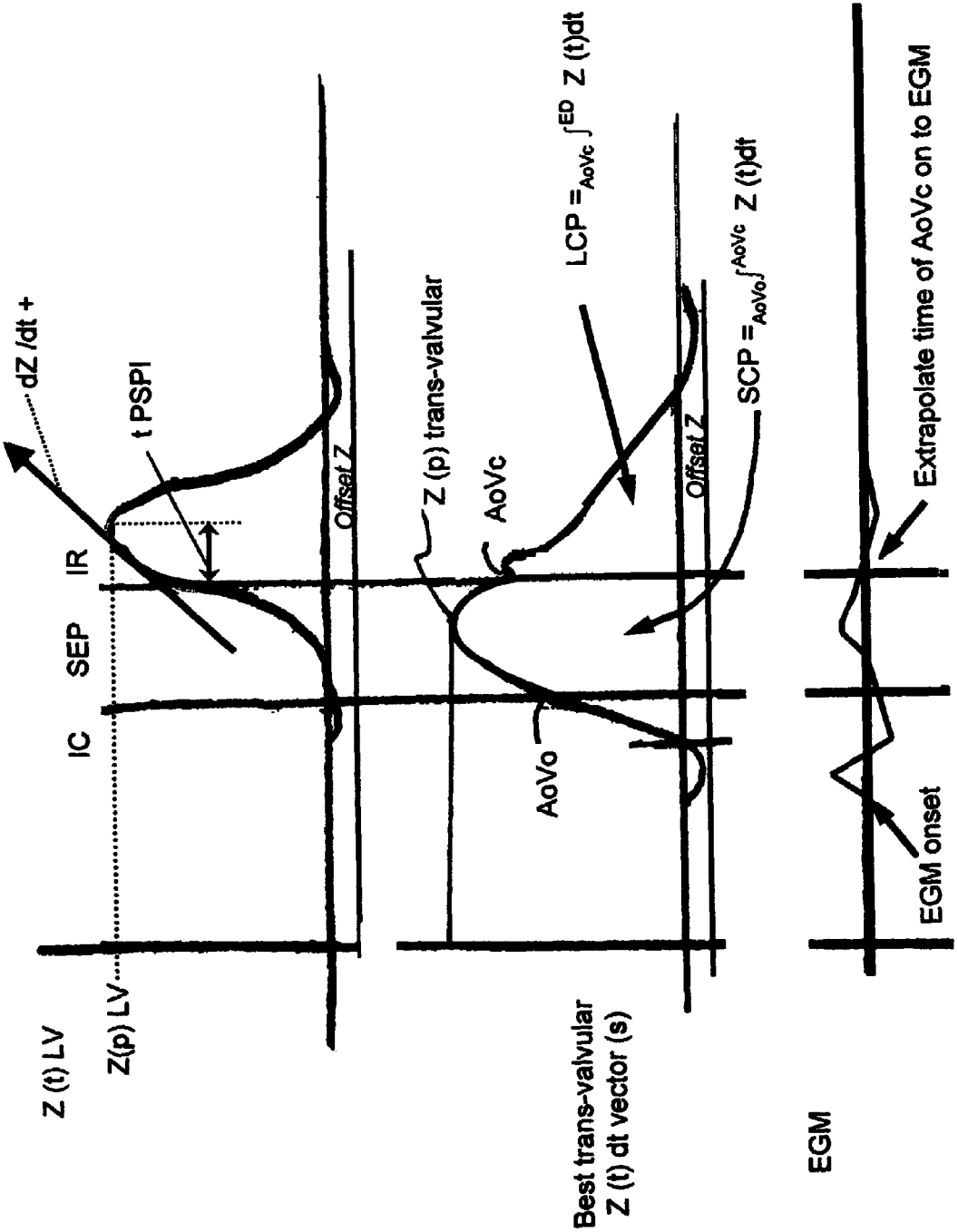
FIG. 12 illustrates various parameters of Global Cardiac Performance based on varying time limits for integration.

Global Cardiac Performance (GCP) is determined from internal electrode pairs/combinations (multipolar) that traverse the heart and are typically positioned at locations that allow for an evaluation of changes in impedance over time in multiple vectors. These electrodes are used to generate multipolar impedance waveforms and may be derived by simultaneously using multipolar electrodes for current delivery and measurement of voltage or techniques of summation averaging of regionally sampled impedance data (using a variety of vectors) over multiple cardiac cycles under similar conditions (e.g. heart rate, end expiration). These multipolar waveforms are less subject to signal disturbances associated with segmental myocardial impairments and delays in regional contraction, which are manifested in waveforms derived from a single vector. Analysis of the Global Cardiac Performance data can also include parameters of peak impedance, first and second order derivatives and time to peak impedance. The latter parameter requires the least amount of signal fidelity and is most useful for comparisons of time of peak contractility in dysynchronous myocardial segments (FIGS. 9 and 12).

Such morphologic characteristics will ideally provide information on systolic and diastolic properties of the patient's cardiac system. Integration techniques may be used during specific intervals of the cardiac cycle (e.g. systole), preferably defined by valvular events (e.g. aortic valve opening and closing).

Figure 10:
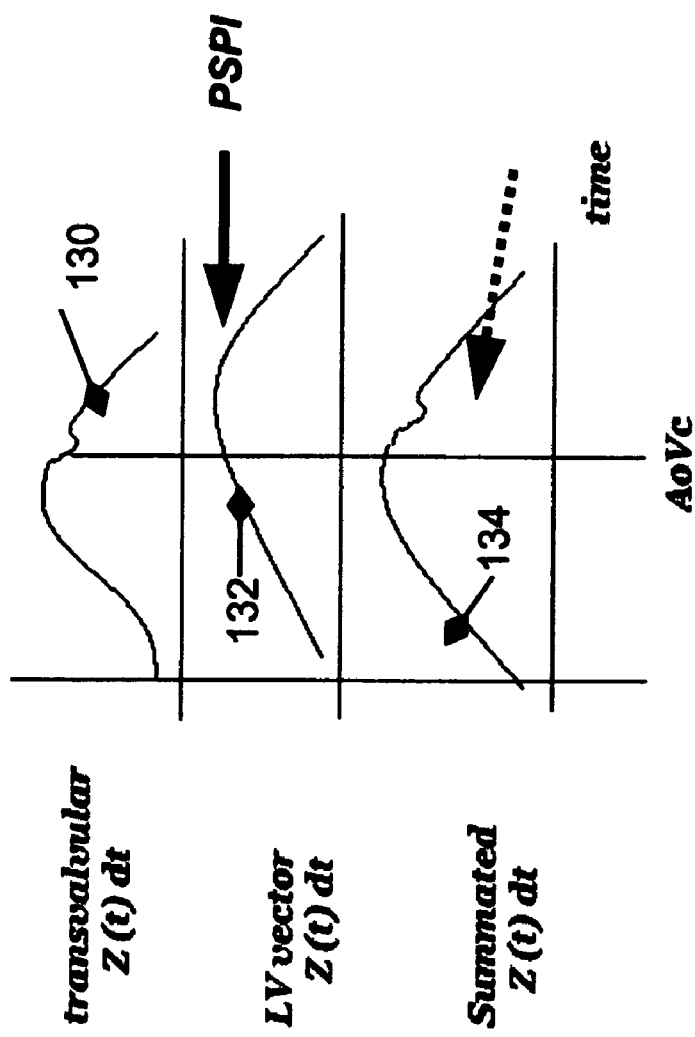
FIG. 10 shows impedance waveforms derived from RV trans-valvular electrodes and LV electrodes which have been summated to derive a more global representation of cardiac performance and dysynchrony.
Figure 11:
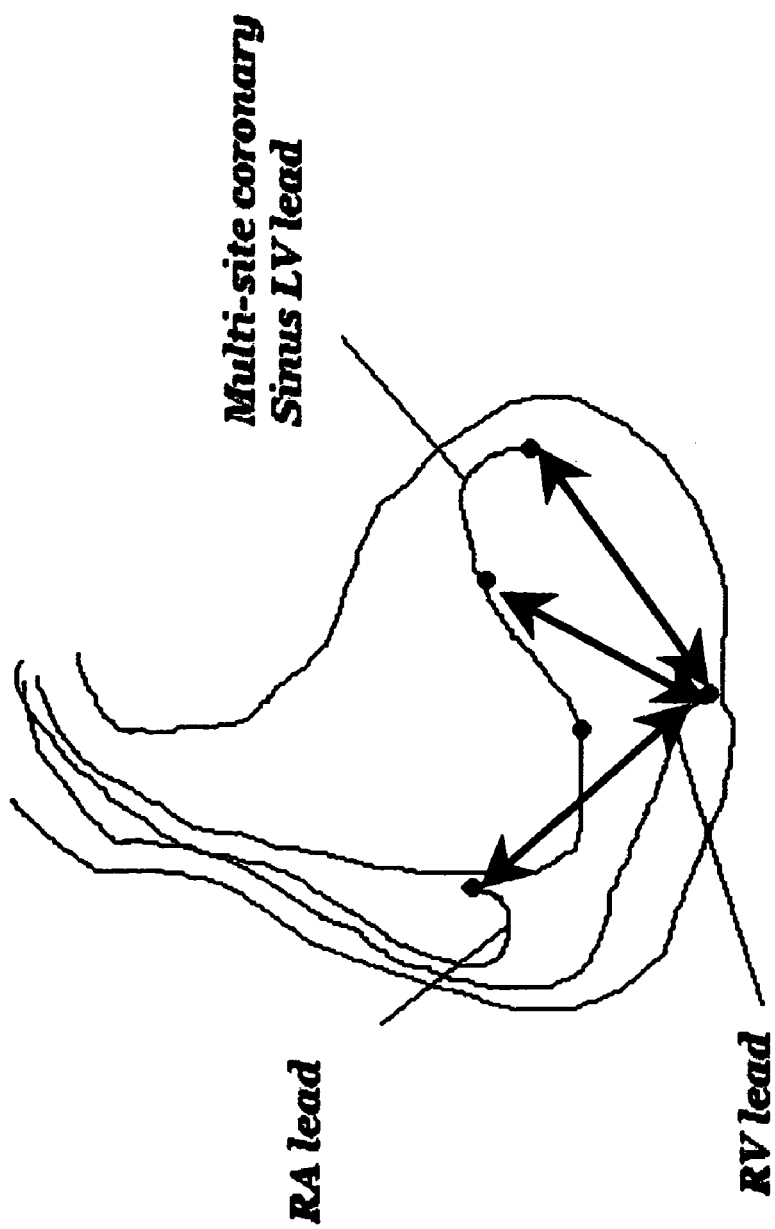
FIG. 11 is an illustration of multipolar impedance signals from triple integration techniques of data acquired in 3 dimensions.

In situations where Z(t)dt is of greater fidelity, more specific information that relates to systolic and diastolic myocardial properties may be derived from the impedance waveform rather than, for example, the time of peak impedance or value of peak impedance (FIG. 5). Such waveforms can also be derived from regional impedance waveforms between one set of electrodes but if possible the data should be reflective of changes in impedance, Z(t)dt, in a global fashion (Global Cardiac Performance) between multiple electrodes (multipolar). Multipolar data acquisition can, but need not, occur simultaneously. For example, right heart Z(t)dt (RA ring and RV tip for current delivery electrodes with RA tip and RV ring as voltage measuring electrodes for derivation of impedance) can be acquired over C cardiac cycles with ensemble averaging techniques. This can then be repeated between the LV and RV apical electrodes and SVC and LV electrodes in a similar fashion. This data can be used for defining regional properties (RA to RV tip representing RV and LV inferior-basal wall) or global properties by summation averaging or integration of regional impedance waveforms as to derive global impedance waveforms (FIGS. 10 and 11). The more global the representation of impedance data, the more information is obtained that relates to both overall cardiac performance and dysynchrony.

Systolic Cardiac Performance

Pure systolic function can be described using impedance data gathered during myocardial thickening. This can be defined as systolic cardiac performance, SCP. Integration of impedance from the onset of systole (or ideally time of aortic valve opening) to time of peak contractility (or ideally aortic valve closure) in one or more vectors would be a specific means of accomplishing this (FIG. 12):

$$SCP(t) = \int Z(t)dt \qquad \text{Equation 3}$$

where t is either measured from onset of systolic contraction, t=0, to peak contraction, t=p or preferably during the systolic ejection phase if aortic valve events are defined.

Lusitropic Cardiac Performance

Integration of impedance during diastole will yield data relevant to myocardial relaxation. This would represent the diastolic or lusitropic cardiac performance, LCP (FIG. 12).

$$LCP(t) = \int Z(t)dt \qquad \text{Equation 4}$$

The time frames for integration will be between aortic valve closure and onset of myocardial thickening as defined by onset of dZ/dt+. Alternatively (if valvular events are not defined), it can acquired between time of Z (peak) and Z baseline, though this would also comprise impedance values related to myocardial thickening and be less pure. Optimal lusitropy or diastolic relaxation should occur in short order without post-systolic thickening. Post-systolic thickening is an ultrasonic marker of diastolic abnormalities and in its presence, LCP will be a greater value as myocardial segments which are thickening after aortic valve closure will increase impedance values when dZ/dt− should be a steeper negative slope. Measurements of dZ/dt itself after Z (peak) [dZ/dt$^-$] can also be used for assessment of lusitropic properties and incorporated into such analysis much in the same way dZ/dt+ relates to systolic properties.

As a larger area under the initial portion (or ideally during the systolic ejection phase) of the impedance curve will denote better systolic cardiac performance, a smaller area under the latter portion of the impedance curve will indicate more optimal lusitropic properties without regional post-systolic myocardial thickening (i.e. post-systolic positive impedance, PSPI). In circumstances where there are regional delays in myocardial thickening the value of LCP will increase secondary to post-systolic contractility in dysynchronous segments (FIG. 10). Ideal representation of this data could be derived by assessing a systolic-lusitropic index, SLI:

Equation 5:

$$SLI = \frac{\int Z(t)dt \text{ systole}}{\int Z(t)dt \text{ diastole}}$$

or

Equation 6: $\quad SLI = SCP/LCP$

As contractility improves the numerator will increase and as lusitropic properties improve the denominator will decrease. As overall systolic and diastolic function is optimized the SLI will increase. Use of other data such as first and second order derivative data or slopes of impedance curves during systole and diastole would provide complementary information which can be independently evaluated or even incorporated into equations relating to cardiac performance as well.

Defining the time of aortic valve opening and closure on the impedance curve (potentially visible as notching) will be better defined with higher frequency current pulses as to better delineate systolic and diastolic time frames and more importantly, allow for the determination of post-systolic myocardial thickening, PSMT. One can reduce and potentially eliminate PSMT by delivering pre-excited stimuli based on correction factors obtained in such a fashion. If pre-excitation occurs to the electrode pair which is delayed by t>t PSPI (time of post-systolic impedance) relative to the time where a specific region has an appropriate time of initial depolarization/myocardial thickening, conditions of synchrony are likely to be met (FIG. 12 top).

The vector or vectors from which this data is obtained could represent regional or global properties. If the RV tip to RV coil is used, this data will be more representative of RV function. If the LV tip to can is used this would be more representative of LV function. Use of more than one vector (multi-polar electrodes) would provide more multi-dimensional data and represent global cardiac performance, GCP. This can be represented by using multiple integral equations (e.g. FIG. 11—triple integration).

The above data can be acquired by delivering current pulses between the RV tip and can and measuring voltage between the RV ring and RV coil in order to obtain RV impedance curve data. Similarly, one can deliver current between the RV tip and can and derive impedance curve data using voltage measured between the RV ring and LV tip. Delivering current between the RV tip and SVC/can electrodes while measuring voltage between the RV ring and RV coil as well as RV ring and LV tip would provide more global data either with or without use of multiple integrals. Multiple methods and vectors can be used for delivering current, measuring voltage, and deriving impedance curve data. The general principle is that this technology can be used for both regional and global assessments of cardiac systolic and diastolic properties as described above. Such data can be used for monitoring purposes (Vital Monitoring System) and for assessing optimal timing intervals for multi-site resynchronization devices. Multi-polar impedance data is best suited for evaluation of Global Cardiac Performance and should be incorporated into algorithms that comprise the closed loop control system whenever possible.

In one embodiment, significant deterioration in parameters of Global Cardiac Performance can modify device therapy algorithms (e.g. defibrillate rather than anti-tachycardia pacing) or trigger a search for undetected ventricular arrhythmia (slow ventricular tachycardia). Changes in the morphologic characteristics of multi-polar impedance waveforms can serve the same purpose. As pressure volume loops obtained from hearts with and without dysynchrony in normal sinus rhythm and ventricular tachycardia are representative of such properties ((Lima JA. Circulation 1983; 68, No 5. 928–938), impedance signals will also depict similar pathophysiology (FIG. 13).

In another embodiment, data related to respiratory status (e.g. increases in minute ventilation, decreases in transpulmonic impedance) and/or findings consistent with impairments in cardiac performance (e.g. decreases in SLI, changes in waveform morphology or decreases dZ/dt etc.) can trigger a Vital Monitoring System (VMS) to search for undetected arrhythmias. If specific parameters exceed or fall below specific values, points can be accrued in a bin counter. If the data points entered into the bin counter meet certain criteria, tachyarrhythmia therapy algorithms can be modified. Examples of such modifications in therapy algorithms include lowering the rate cut off for VT detection, eliminating VT zone therapy and only implement cardioversion therapies (FIG. 14). Conversely, VT exists and impairments in cardiac performance do not occur, more conservative therapies are utilized (e,g. antitachycardia pacing rather than defibrillation, no therapy for slow VT). Bin counter criteria can be individualized such that patients with poorer cardiac reserve will require less impairment in cardio-respiratory status (e.g. lower bin counter point values) before device therapy algorithms are modified. Any significant changes in clinical status can be reviewed at periodic intervals (e.g. office interrogation or via telecommunication) and be stored as trend data. Periodic interval monitoring can occur at specified time frames for gathering of bin counter data points. The frequency of such monitoring can increase if early deleterious changes in a patient's clinical status are suspected based on the VMS bin counter values.

Regional declines in cardiac performance (e.g. RV vector impedance data with decreases in peak impedance and delays in time to peak impedance) can be indicative of a change in clinical status (progression of right coronary artery ischemia). Specific changes can be noted prior to delivery of tachyarrhythmia therapy and direct a physician to perform testing (e.g. coronary angiography). In a preferred embodiment, the Vital Monitoring System can store not only electrogram data but also impedance data in a loop for review each time tachyarrhythmia therapy is delivered and provide the physician with insight into potential causes for ventricular dysrhythmias (e.g. ischemia).

In order to further optimize the clinical relevance of data derived in this fashion, implementation of respiratory impedance data is necessary. This can be obtained by analysis of impedance between the SVC coil and can which reflects peri-hilar congestion. Alternatively, this can be obtained from analysis of baseline offset impedance as described above. Current delivery between the RV coil and LV tip would be somewhat parallel to derived voltage data between the SVC and can and would allow the system to acquire single impulse impedance measurements as well as impedance curve determinations in a peri-hilar vector, though any combination of vectors may be used for either current delivery and voltage/impedance determinations. Use of lower frequency current pulses would serve as a low pass filter reducing the contribution of myocardial properties to such data. One can use any vector to acquire this data though perihilar impedance will be more sensitive. As a more euvolemic state will correlate with higher impedance values, transpulmonic impedance data can be incorporated into the numerator (i.e. multiplication) of the above equations to derive a representation of global cardio-respiratory performance, GCRP:

$$GCRP=[\int Z(t)dt\text{transpulmonic}]\cdot[SLI] \qquad \text{Equation 7}$$

It would be more suitable however to normalize real time Ztranspulmonic to baseline measurements that are made when a patient is clinically euvolemic. Determination of euvolemia can be made with invasive measurements of pulmonary capillary wedge pressure or based on clinical assumptions of fluid status. As such, we define the transpulmonic impedance index, TPI:

Equation 8:

$$TPI = \frac{\int Z(t)dt \text{ transpulmonic (real time)}}{\int Z(t)dt \text{ transpulmonic } (euvolemia)}$$

Isolated measurements of transpulmonic impedance can be made at end expiration and end diastole and averaged rather than by integrating the offset impedance over a specific time frame. Incorporation of this data into equation 4 yields a more appropriate representation of GCRP:

$$GCRP=(SLI)\cdot(TPI) \qquad \text{Equation 9}$$

where TPI reflects transpulmonic impedance in real time normalized to euvolemic transpulmonic impedance. Euvolemia can be most easily and accurately determined by using the greatest value of transpulmonic impedance (lowest thoracic fluid volume) since the prior time of periodic interval monitoring. It is worth mention that lower values of transpulmonic impedance (increased thoracic fluid content) may result in better cardiac performance as a result of more optimal Starling's forces seen with slight elevations in pulmonary capillary wedge pressure and LV end diastolic pressures. In one embodiment, this optimal transpulmonic impedance value can be derived at a time when patient has had invasive monitoring of such clinical variables or by correlating the optimal transpulmonic impedance value to a time when measurements of Global Cardiac Performance are ideal (e.g. SLI).

Changes in transpulmonic impedance that occur with variations in heart rate and respiration need to be accounted for. This can be done by triggering acquisition of impedance data for calculation of these indices during similar conditions (e.g. same heart rate and minute ventilation).

Graphic representation (trend data) of GCRP, SLI, TPI, SCP and LCP will allow the practitioner to make valuable clinical assessments between office visits. Such data can be averaged over 24 hour periods (or other time frame) using periodic interval monitoring. PIM can also be used as part of the control system where the effects of changes in interval timing are analyzed using any of the GCP parameters described above. Such analyses need to account for heart rate. Ideally, measurements made through PIM can be done under similar conditions (e.g. end-expiration). This will improve signal to noise ratios and allow for appropriate comparisons.

Stochastic Optimal Control System

The control system evaluates a family of variables as to achieve the outcome of improving a patient's congestive heart failure symptoms and long-term prognosis. Such a control system falls into the category of a Stochastic Optimal Control System (FIG. 15). In order to achieve optimal control, the system must recognize disturbances such as impairments in impedance signal fidelity. Multivariate statistical analysis techniques (described below) will serve this purpose. Controllable inputs to the system are changes in interval timing. Uncontrollable inputs are respiration, cardiac translation and patient movement. Use of blended sensors to determine time of data acquisition and determination of time frames of cardiac translation where data sampling is minimized will help optimize the control system. In this fashion, the dynamic states measured by the system (e.g. Z(t)dt) and derived parameters (e.g. GCP) will be utilized as to direct programming of interval timing as to optimize process outputs (e.g. cardiac performance, resynchronization) and improve clinical outcome.

Morphologic Determinations of Impedance Signal Adequacy

Impedance waveforms have a variety of morphologic characteristics. In the normal heart, specific vectors or electrode combinations have specific appearances. In the pathologic heart, morphologic changes in the impedance waveform will be found. For example, lower peak impedance values and decreases in positive peak dZ/dt will be seen in infarcted myocardium. Comparisons of individual impedance morphology to templates derived from normal and abnormal individuals can be made if such template data is stored in a data bank within the device. Determination of how specific impedance waveforms relate to myocardial contractile properties can be made through connectivity with an echo interface. Multivariate statistical analysis can be implemented using analysis of variance methods or other techniques. Equations which describe acquired waveforms, first and second order derivative data, and integration techniques can be stored in the data bank and used for analysis. Characteristics of waveform continuity and symmetry are examples of how descriptive equations relate to the impedance signal. Discriminant analysis is one example of how statistical analysis can serve to evaluate impedance waveforms.

Discriminant Analysis of Signal Vectors

Once data acquisition is completed for any electrode combination(s) the impedance waveform(s) are analyzed for determining which signals are adequate for purposes of monitoring and directing interval timing. The costs to the system may be less if specific vectors or vector combinations are evaluated for adequacy one at a time. Conversely, the evaluation process can occur for all waveforms acquired and a final decision can be rendered as to which waveforms are adequate and are representative of the most clinically useful data for further signal processing and implementation in the closed loop control system.

Determination of ideal vectors for data acquisition can be made at the time of initial data entry and/or with use of echo interface. The ideal control system can make the same determinations by analysis of impedance signals through comparisons to morphologic template data without an echo interface (Morphologic Determination of Impedance Signal Adequacy) or by using methods of multivariate statistical analysis. In one embodiment and by way of example, Discriminant analysis of impedance waveforms derived from multiple vector combinations lead to selection of optimal electrode configurations for data acquisition. Such selection criteria may vary with exercise. These electrode combinations need not vary during the life of the device/patient but situations may arise where such configurations become inadequate. Such circumstances might include progressive fibrosis which impairs the electrode/myocardial interface, or affects secondary to remodeling or infarction.

Inputs to the Discriminant Analysis algorithms can include a multitude of impedance data (e.g. single vector impedance waveforms or multipolar impedance waveforms subjected to ensemble averaging, or variable multiple vector impedance waveforms subject to summation averaging techniques). Predictor variables are used to assess the adequacy of such impedance data (FIG. 16). These predictor variables may reflect properties including but not limited to fidelity, morphology, and timing. Such predictor variables can be weighted so that the most relevant inputs are weighted higher.

Discriminant Analysis Equation: Discriminant function=$L = b1x1 + b2x2 + b3x3 + \ldots bnxn$ \hfill Equation 10

Discriminant function, L, describes signal fidelity. Values of L over a specific number will indicate adequate signal fidelity. Predictor variables x1–xn are weighted according to relative importance for being able to discriminate high from low fidelity signals. Predictor variable x1 is most important, weighted the highest, and as such b1 is greater than b2–bn.

One example of a predictor variable can be the standard deviation of the integral during systole of sequentially acquired impedance signals in a particular vector (x1). If the standard deviation of this integral is low, this suggests that the acquired signal has limited variability and is less subject to disturbances which would degrade signal fidelity. As this is of greater importance for determination of signal adequacy than other predictor variables the value of b1 would be greater than b2–bn. Other examples of predictor variables include, but are not limited to, beat to beat similarity in impedance waveform morphology. A waveform which is inconsistent from one heartbeat to the next is inadequate. Acquired impedance waveforms can be compared to stored data bank or template waveforms that are known to be high fidelity. Such a comparative analysis is used to determine which signals are adequate for output from the Discriminant Analysis algorithms as well. If the impedance signal derived from one particular vector or from summation of signals derived from 2 or more vectors (summation averaging) are input to the Discriminant Analysis and are determined to be inadequate the control system would not use this data for analysis. Impedance waveforms, whether derived from a single electrode pair (regional) or a combination of electrode pairs (Global Cardiac Performance) that are of adequate fidelity, will be output as adequate and used as part of the control system. In this fashion the system will determine which vectors to use for data analysis (monitoring or to direct timing of CRT). The particular electrode combinations which yield optimal signals will vary from patient to patient. This technique will provide for an individualized means of determining which electrode combinations should be used on a regular basis for measurements of impedance waveforms and will be adjusted if conditions change.

The outputs will be grouped into either adequate or inadequate impedance signals. Under ideal circumstances multiple vectors (electrode combinations) can be used for output data. This output data can be part of the Vital Monitoring System and also be used for programming CRT interval timing. Integration of individual vectors representing 3 dimensional spatial patterns will generate global impedance waveforms, Global Cardiac Performance. Such waveforms will be less prone to extraneous noisy signals especially when techniques of regional ensemble and global summation averaging are utilized. Regional impedance signals will provide more specific information about segmental myocardial abnormalities if the signal to noise ratios is optimal and can ideally be utilized in addition to Global Cardiac Performance data in a complementary fashion.

Temporal Calculator

Figure 17:
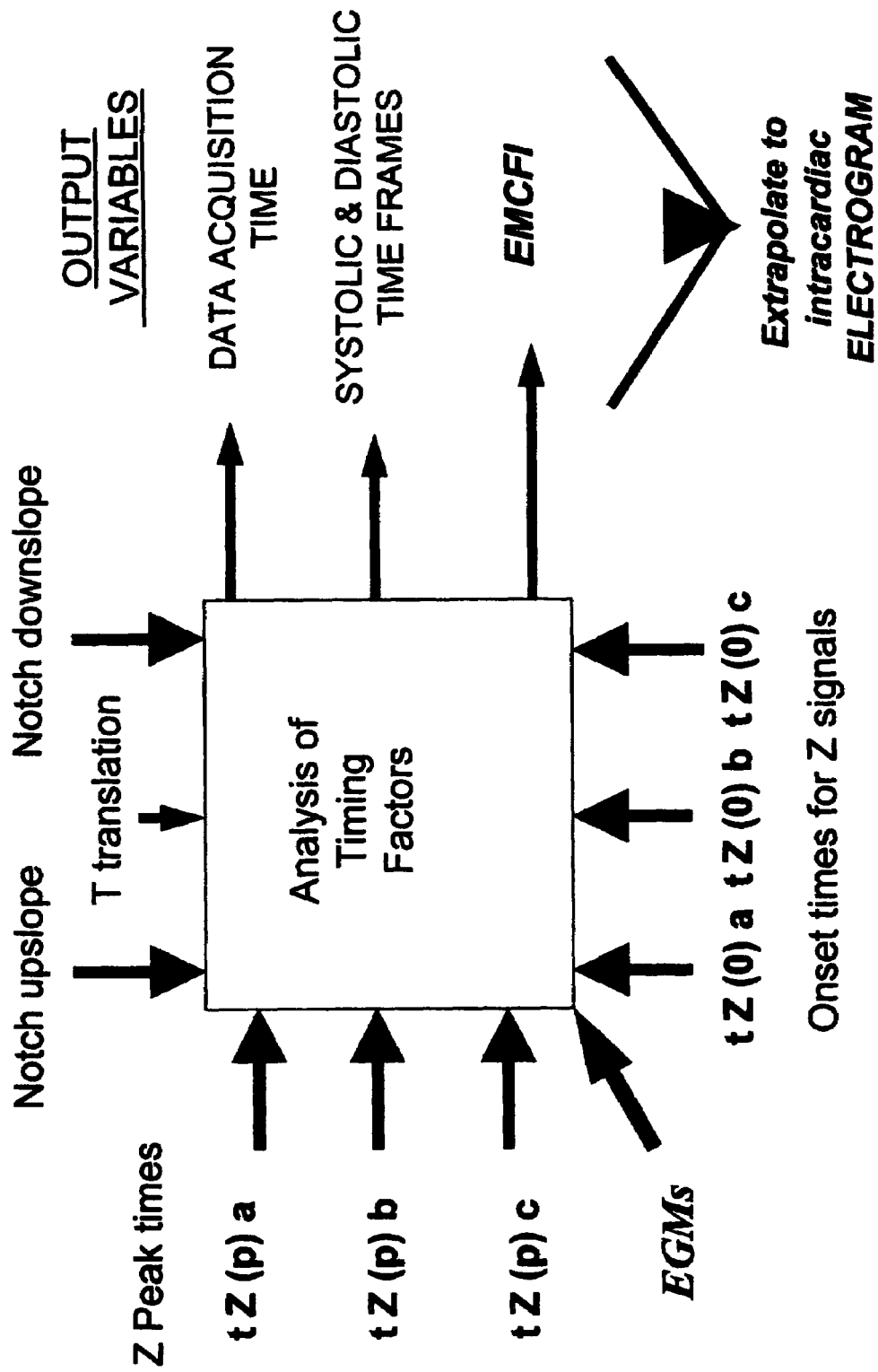
FIG. 17 is a temporal calculator which receives a spectrum of timing data during the cardiac cycle related to intracardiac electrograms and impedance signals and extrapolates this data for reference purposes to the intracardiac electrogram.
Figure 18:
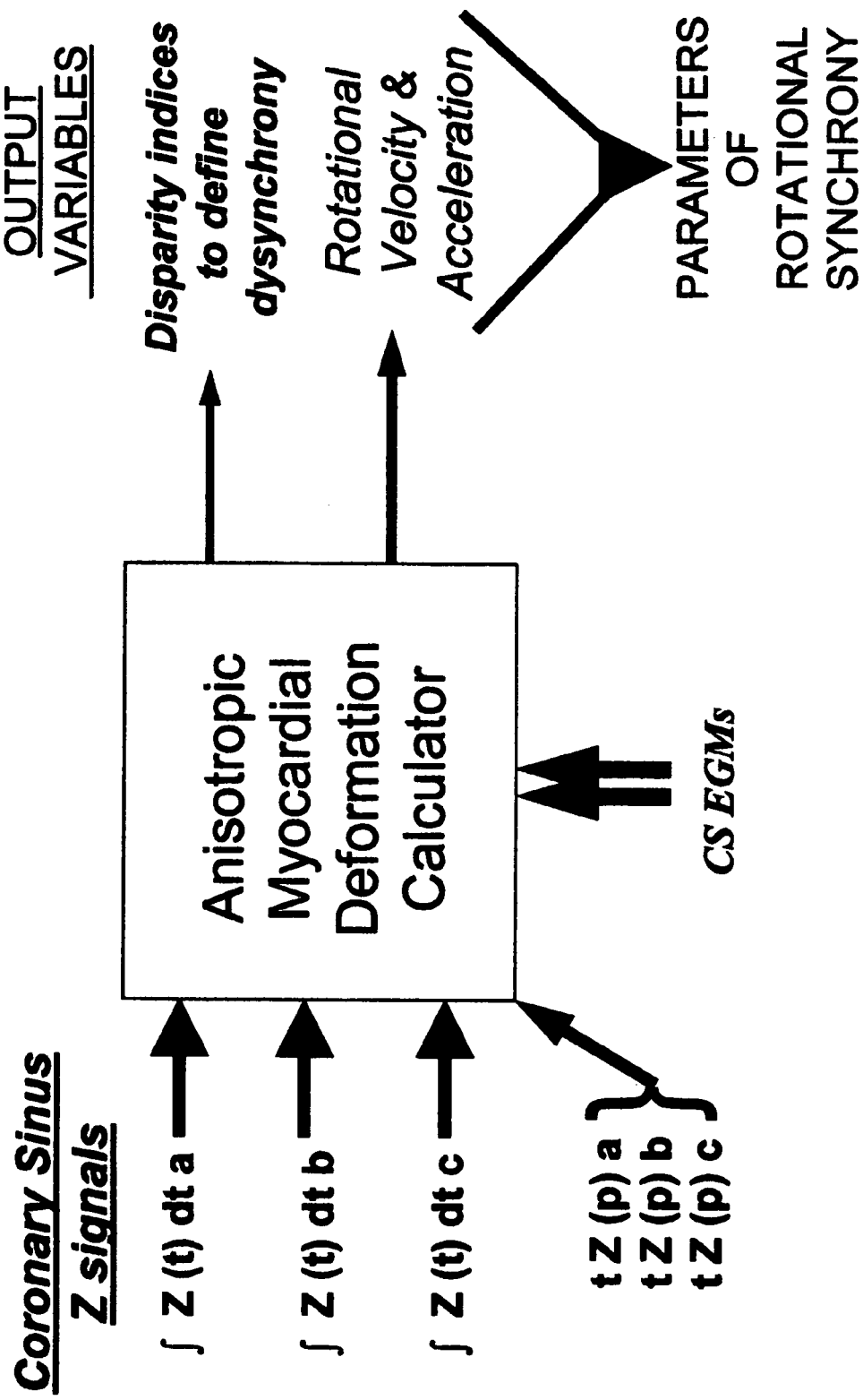
FIG. 18 depicts another calculator that describes anisotropic electro-mechanical properties derived from intracardiac electrograms and impedance signals. The output variables are representative of dysynchronous cardiac properties and can be used in the control system as to evaluate degrees of resynchronization.

Once the highest fidelity impedance data which is deemed adequate with Discriminant Analysis is identified, calculations of event timing can be made with the Temporal Calculator (FIG. 17). This is used for timing of signal acquisition/processing, defining systolic and diastolic time frames and extrapolating specific events to time points on the intracardiac electrogram signal(s). These referenced time points and time frames are then integrated into the closed loop control system for programming of interval timing. Properties of dysynchrony derived from multi-site CRT lead systems which relate to anisotropic myocardial deformation can be entered into a similar calculator and used for closed loop control as well (FIG. 18). These are discussed in the parent application Ser. No. 10/779,162.

Figure 19:
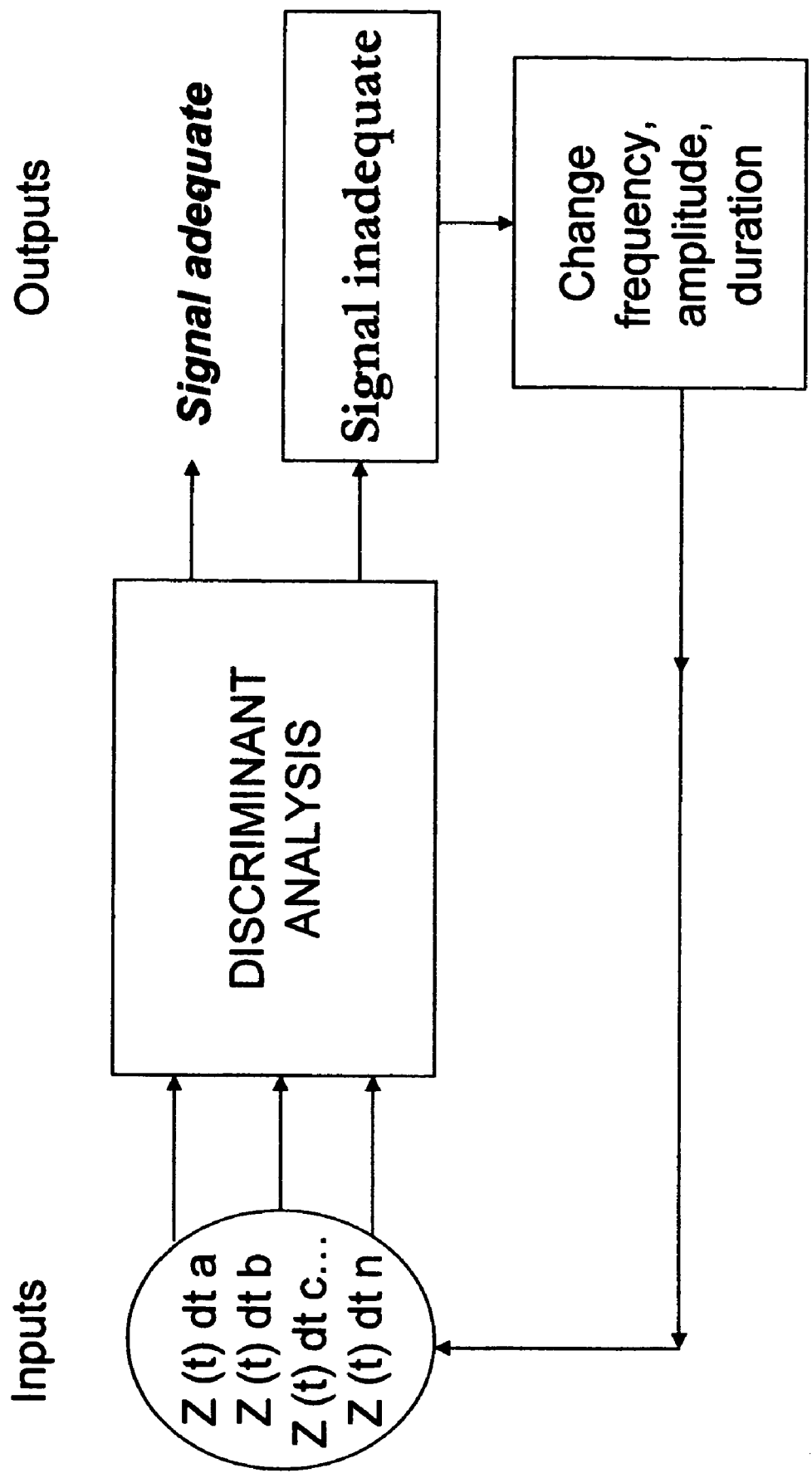
FIG. 19 shows how changes in current frequency, amplitude and pulse width can be modified in circumtances where impedance signals are inadequate for implementation in the control system.

In one embodiment, if signals obtained in various vectors/vector combinations are deemed inadequate by Discriminant Analysis, changes in current stimulation frequency, duration (pulse width) and current amplitude can occur with repeat analysis of signal fidelity (FIG. 19). Such changes in stimulation values can lead to an increment or decrement in the original value by either a default or programmable percentage of the initial settings.

Dynamic Control System/Choosing Highest Fidelity Signals

Figure 20:
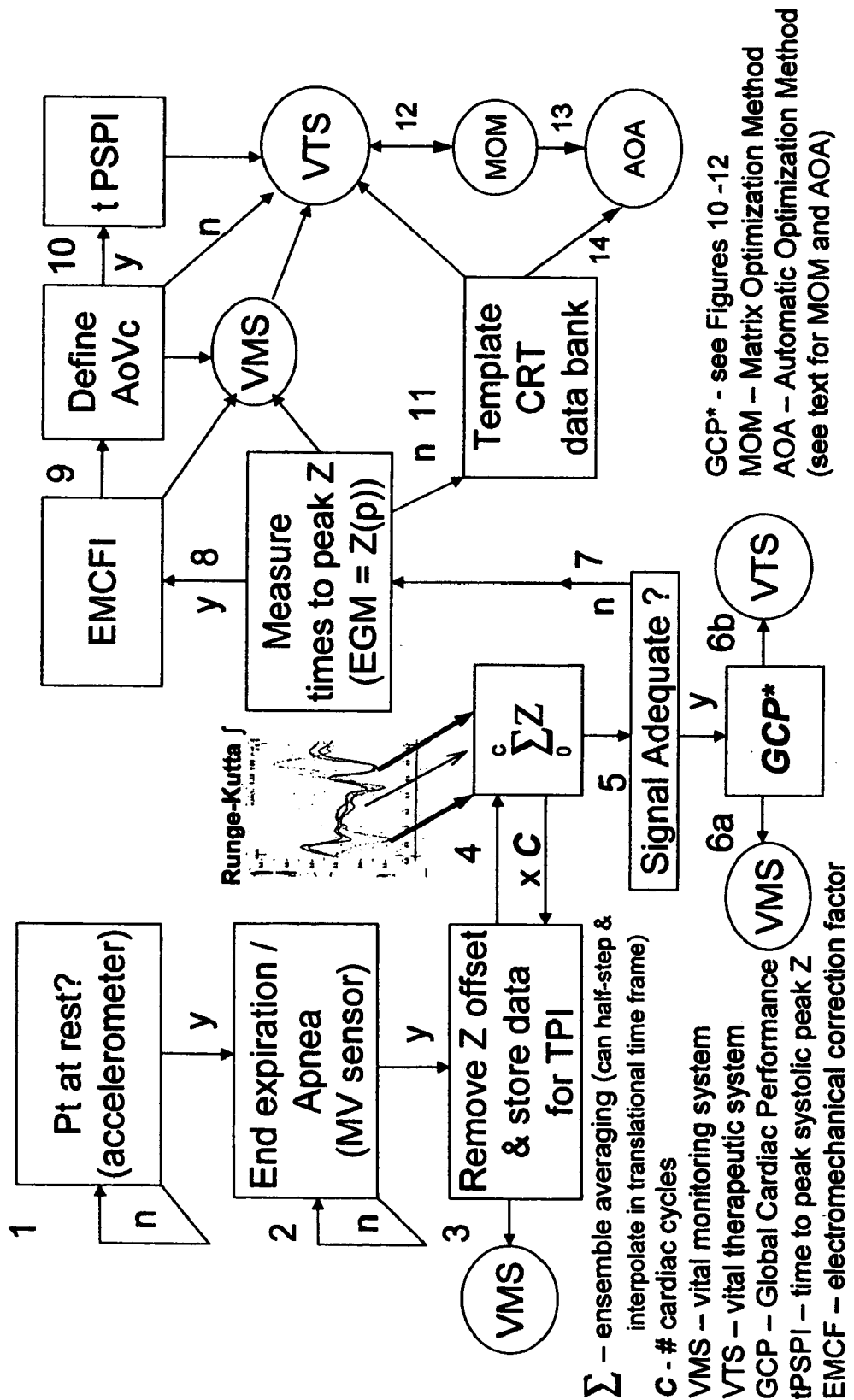
FIG. 20 illustrates how the dynamic control system acquires impedance data, determines signal adequacy and chooses which parameters to use for optimization of enterval timing and monitoring purposes.
Figure 21:
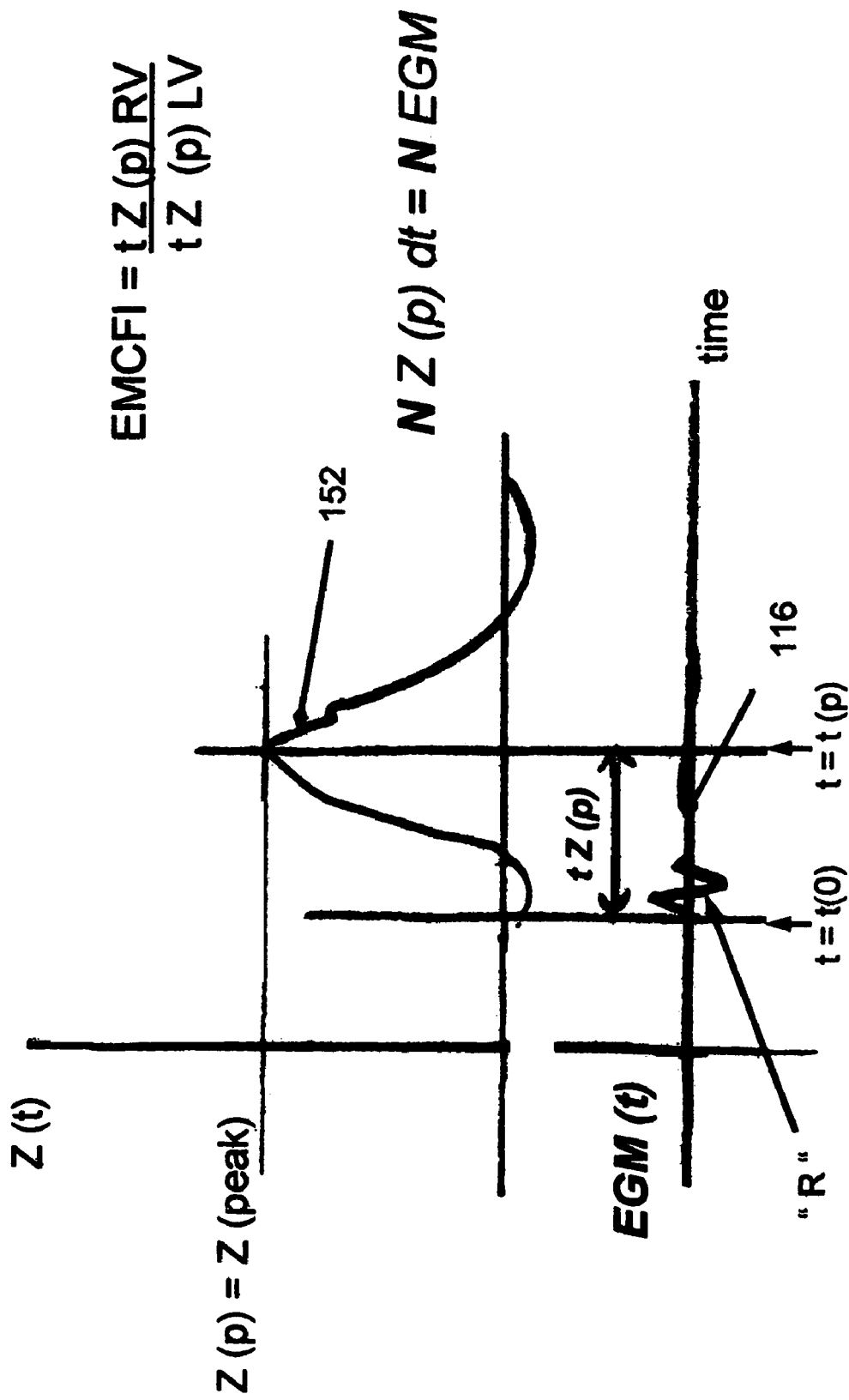
FIG. 21 depicts how the electro-mechanical correction factor is derived from the impedance waveform. The number of impedance waveform peaks, Z(p), is compared to the number of intracardiac electrogram "R" waves as to conform that time to peak impedance can be used as a parameter for directing interval timing.

After determining which electrode combinations yield adequate signals using Discriminant analysis the system chooses which impedance waveforms are used for monitoring purposes and directing interval timing of the CRT. This is depicted in FIG. 20 with steps further detailed in FIG. 20a. In step 1 and 2 blended sensors determine when signals are acquired. In step 3 the impedance offset related to "static" cardiothoracic conditions is removed and stored for monitoring (VMS) and calculation of the transpulmonic impedance index. A specific number of cardiac cycles, C, are used to perform ensemble averaging in step 4. In step 5 Discriminant analysis or other techniques using multivariate statistical analysis is used evaluate the impedance waveforms derived thus far and confirm that the system can derive parameters of Global Cardiac Performance using integration techniques. Such signals ideally will be able to have integration techniques applied for derivation of data representative of systolic and diastolic time frames (e.g. SCP and LCP). If the signal morphology is adequate then the system uses the waveform for monitoring purposes (VMS) and to direct CRT timing (VTS), steps 6a and 6b. If the signals are inadequate then the system will utilize a lower fidelity signal which will be used to direct CRT interval timing (step 7). In the example shown in FIG. 20 the Dynamic control system will utilize time to peak impedance derived from different electrode combinations in a biventricular CRT device (e.g. RV tip to RV coil and a bipolar LV lead). Confirmation that the signals are adequate for such a lower fidelity analysis is made by a counter which compares number of peak impedance events to sensed "R waves" derived from intracardiac electrograms in step 8 (FIG. 21). The electromechanical correction factor index can then be calculated. Once this is calculated the dynamic control system assessed the nature of the notch in step 9. If the time of aortic valve closure can be determined (e.g. trans-valvular electrodes) this is extrapolated to the intracardiac electrogram for reference purposes. In step 10 the system calculates the time of post systolic positive impedance in RV and LV vectors. If, for example, the LV impedance signal is delayed ms milliseconds, pre-excitation of the LV will occur until ms≦0. If the time of post systolic positive impedance can not be determined as the time of aortic valve closure is indeterminate the system changes interval timing until the EMCFI approaches unity. This processing can require determinations of peak impedance during intrinsic rhythm and during pacing.

Figure 26:
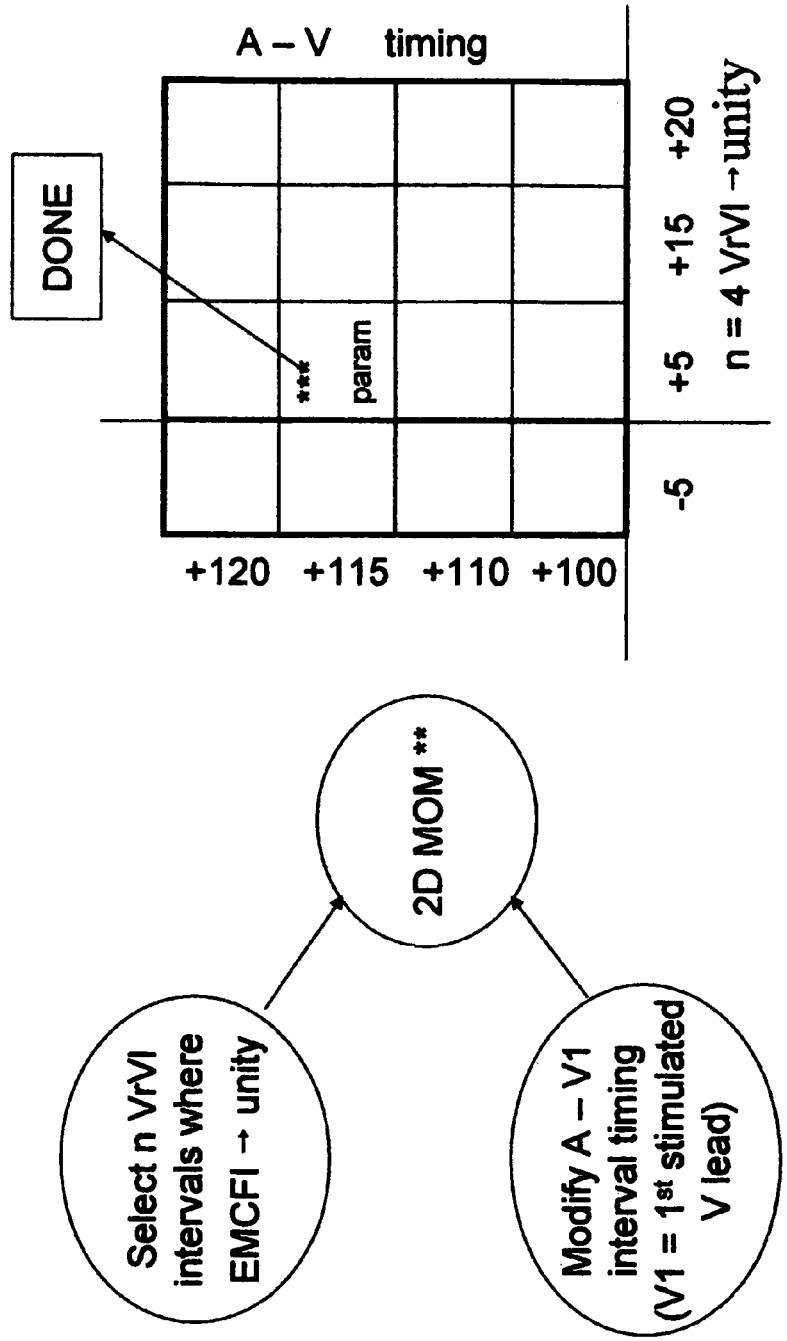
FIG. 26 shows how interval timing in a CRT device is chosen by using the Matrix Optimization Method as to derive which combination of AV and RV-LV intervals optimize a specific cardiac performance parameter.

If the signals are inadequate for measuring peak impedance (poor fidelity), the system will choose a specific set of interval timings from a data bank. This set of interval timing can be chosen from pre-determined values derived from the last evaluation using echo interface or based on comparisons of low fidelity signals to template signals which are associated with similar impedance signal morphology and have been used to have successfully directed programming of CRT interval timing in the past (such comparisons can be for the specific implanted patient or based on data bank templates derived from other patients). After interval timing has been determined using any of these techniques it is further analyzed using the Matrix Optimization Method (step 12) if additional permutations of interval timing need to be evaluated (e.g. AV interval or additional intra-ventricular intervals in a multi-site LV lead). Such interval timing can thus be fine-tuned, for example, by choosing a number of combinations of timing where EMCFI approached unity and a predetermined number of AV intervals (e.g. based on echo AV optimization performed in the past) as described in the parent application, patent application Ser. No. 10/779,162 (FIG. 26). After the MOM directs programming of interval timing associated with optimal conditions the Automatic Optimization Algorithm serves to periodically evaluate the effectiveness of such chosen interval timing at periodic intervals (step 13 and 14).

Automatic Optimization Algorithm

Figure 22:
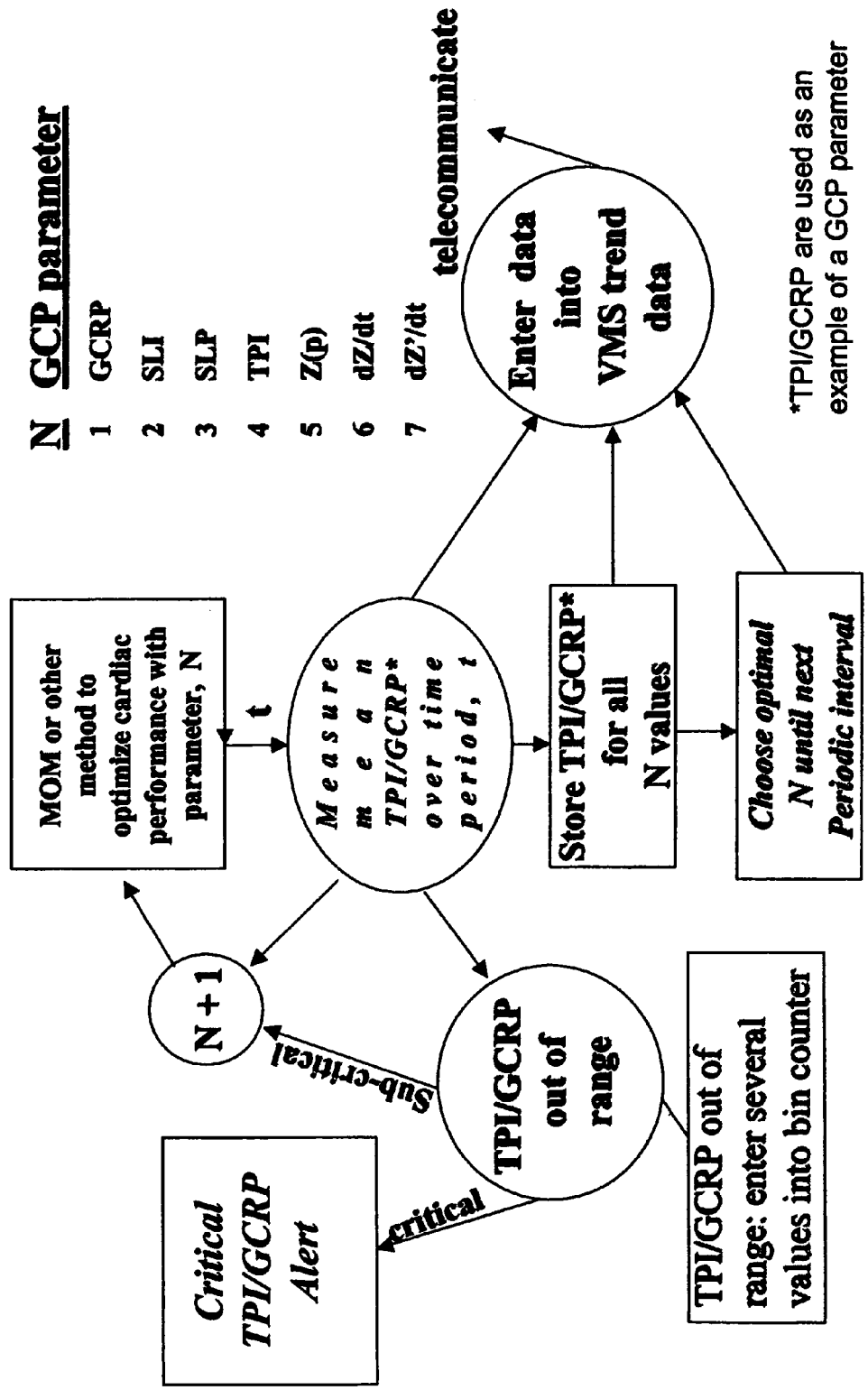
Figure 22:
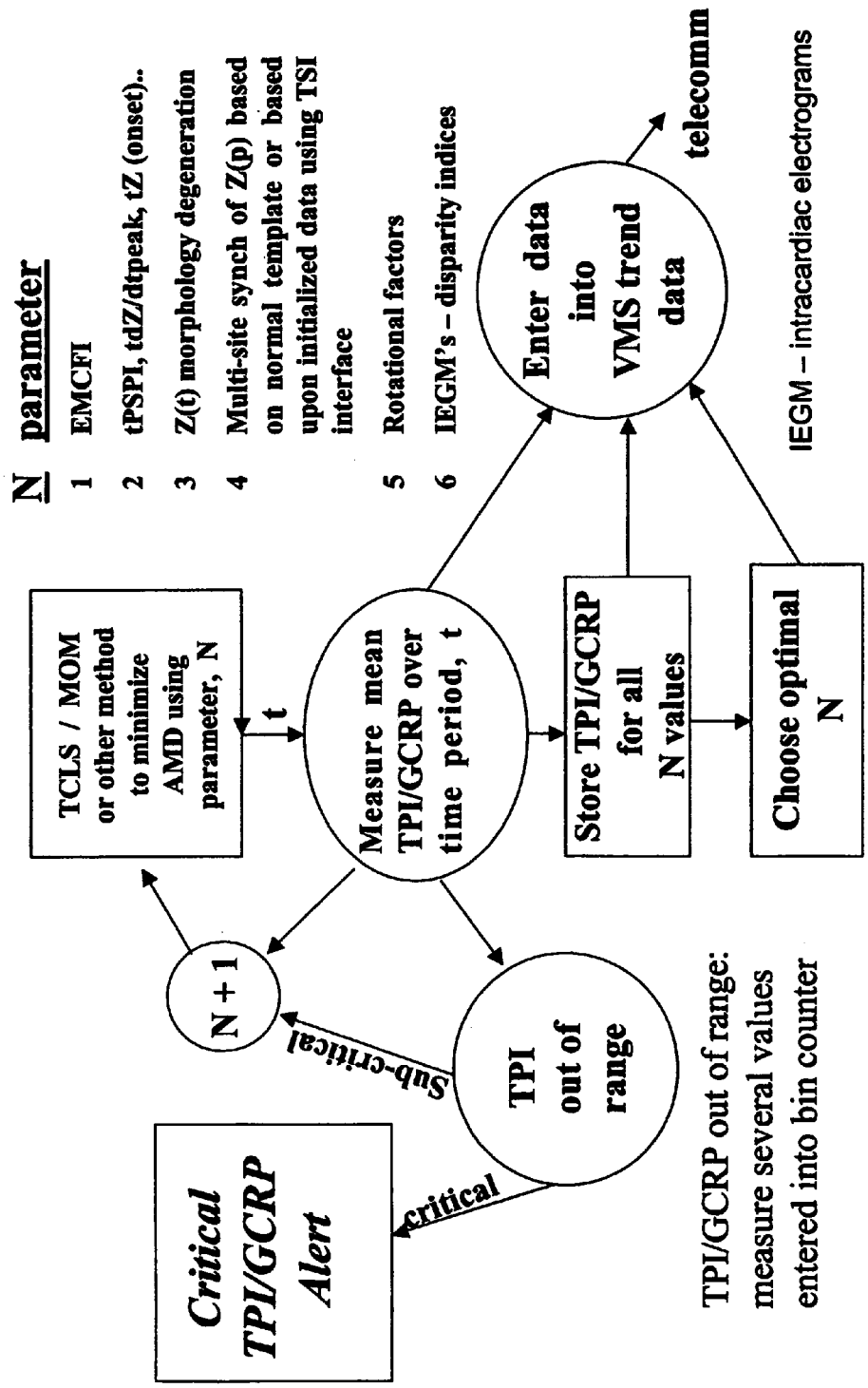

Automatic Optimization Algorithms (AOA) evaluates the effectiveness of programmed CRT interval timing over specific intervals of time and serves as an overseeing control system. The AOA can evaluate Global Cardiac Performance using intrinsic measurements of impedance (e.g. dZ/dt, peak Z, integrals of Z(t)dt with varying limits, Z offset (thoracic fluid volume)). This is described in detail in patent application Ser. No. 10/779,162 and is depicted in FIGS. 22a, b and c. Which parameters are evaluated depends on signal fidelity as discussed above. The AOA can parameter switch as needed though the clinically most useful parameter should be utilized whenever possible (e.g. GCRP). Discriminant analysis or other techniques will serve to direct the switch of parameters utilized in the control system. Parameters such as EMCFI desribe dysynchrony. Time to peak dZ/dt and time to onset of Z(t)dt are alternate parameters of dysynchrony that can be used if the time of the peak impedance value can not be defined. Ideally parameters representative of Global Cardiac Performance that relate to synchronization and cardiac performance can be utilized (FIG. 22a). Parameters that describe timing and synchronization alone (FIG. 22b) will be suitable but do not represent as much clinically relevant information. In circumstances where no parameter can be used because of inadequate impedance signals, specific sets of interval timing may be tried over specific time frames while trends in transpulmonic impedance are evaluated (FIG. 22c). In this situation the MOM will not be utilized (Motherless Option) as no cardiac performance parameter can be optimized.

If a sub-critical circumstance arises then the Automatic Optimization Algorithm will cause a parameter switch so that a different parameter is used for overseeing the system which may be more effective for evaluation of the clinical response to CRT interval timing. Such parameter switching may be necessitated if signal fidelity does not allow use of a specific parameter as well. The AOA can modify interval timing to a default setting or if a critical circumstance arises an emergency default pacing modality can be implemented.

Vital Therapeutic System—CRT Interval Timing

Figure 23:
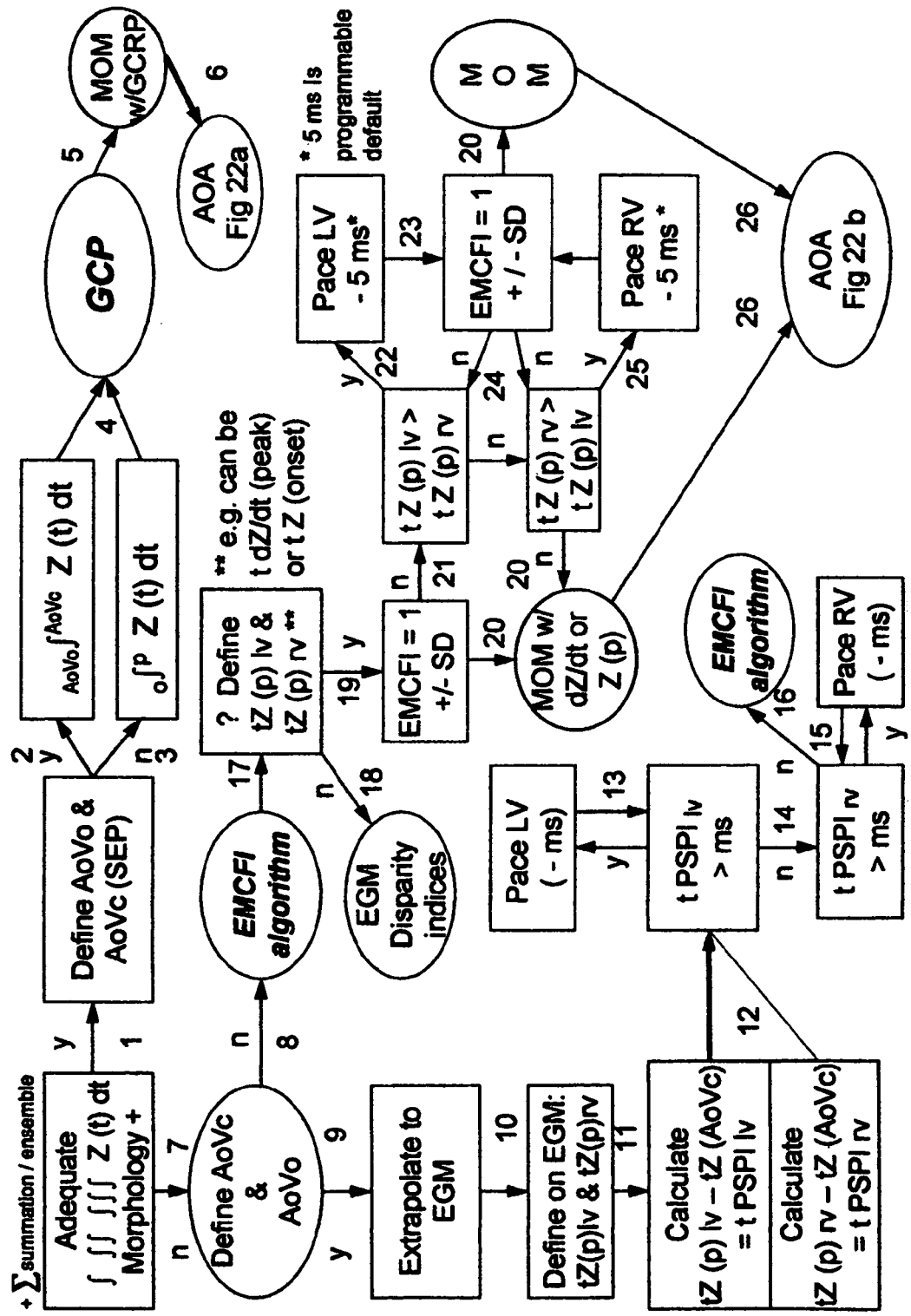
FIG. 23 is a flow diagram for the Vital Therapeutic System, VTS, and details how interval timing is modified using a variety of techniques based on the degree of signal fidelity.

The methodology employed to modify interval timing is illustrated in FIG. 23. This has similarities to the AOA whereby the highest fidelity impedance data yielding the most clinically relevant data is utilized to direct CRT timing. In the circumstance where measurements of Global Cardiac Performance parameters can be utilized (step 1), signals of the highest fidelity, descriptive of Z(t)dt morphology, can be implemented. If valvular events are identifiable (step 2), the VTS will use integration techniques over systole and diastole as to derive parameters of Global Cardiac Performance (step 4). The system will then use such GCP parameters in the Matrix Optimization Method, step 5, and for the Automatic Optimization Algorithm (step 6 and FIG. 22a). The specific parameter optimized, CPPo, will ideally reflect both cardiac performance and dysynchronous properties. If systolic and diastolic time frames can be determined, the parameter used will be the SLI. This data can be supplemented with measurements of the TPI and the GCRP can be used in the best of circumstances. The set of interval timing which maximizes GCRP is then programmed. If needed, parameter switching can occur (e.g. inadequate characterization of diastolic time frames) and a pure measurement of systolic function such as SCP or even Z(p), peak impedance, can be evaluated at any programmed interval timing. If valvular events are not identifiable but the impedance waveform morphology is adequate, integration techniques over relative systolic and diastolic time frames will occur from time of onset of the positive slope (upward deflection) of the impedance signal, Z(0)dt to peak Z, Z(p)dt, and from time of Z(p)dt to the time when Z(t)dt reaches its baseline value, respectively (step 3).

If signal morphology is intermediate but valvular events can be defined (step 7), time of post-systolic positive impedance can be determined and used to make a gross change in interval timing (e.g. pre-excite the appropriate electrode as to cause t PSPI to be $\leq 0$). If valvular events are not identifiable but time of peak impedance is determined then the EMCFI algorithm is utilized (step 8). The EMCFI algorithm is less ideal, for example, as RV and LV timing may be synchronous but after aortic valve closure (global electromechanical delays). Use of additional control systems such as MOM and the AOA will help optimize interval timing programmed in this fashion. The EMCFI algorithm however is capable of more fine tuning than the t PSPI algorithm. After the t PSPI algorithm has caused pre-excited stimulation as to insure stimulation during the systolic ejection period, further optimization in timing can occur using the EMCFI algorithm. The t PSPI algorithm can be ideally implemented at time of initial data entry during intrinsic rhythm and further modifications in interval timing can occur using the EMCFI algorithm thereafter.

Eliminating Post-Systolic Positive Impedance Time (t PSPI)

In step 9 time of aortic valvular events are extrapolated to the intracardiac electrogram, IEGM, used as a reference. In step 10 time of peak impedance in the specific vectors subject to synchronization (e.g. LV and RV) are extrapolated on the reference IEGM. A calculator then determines the t PSPI for each vector in step 11. In steps 12–15 changes in interval timing for stimulation of electrodes in these vectors occur until peak myocardial impedance is no longer post-systolic but occurs during the systolic ejection phase (step 16 and FIG. 8). A similar algorithm can be employed in circumstances where there is pre-systolic positive impedance.

EMCFI Algorithm

The EMCFI algorithm will require less fidelity than either the GCP or t PSPI algorithms. This algorithm will necessitate identification of time of peak impedance (step 17). If this is not possible (step 18), the system can use Disparity Indices derived from IEGMs obtained in various vector combinations (see Electrogram Disparity Indices). Once time of Z(p) is determined the system calculates the EMCFI (step 19). If the EMCFI approaches unity (step 20) the set(s) of programmed interval timing that cause EMCFI to approach one +/− a given standard deviation are used in MOM(step 20) with the highest fidelity impedance parameter possible (e.g. Z(p) or dZ.dt). If EMCFI is not close to unity, changes in interval timing occur until EMCFI approaches unity (steps 21–25). After interval timing that corresponds to CPPo using MOM is programmed the AOA serves to oversee the system as an additional control at periodic intervals (step 26).

In an alternate embodiment, equations that describe the relationship between relative times of peak impedance and stimulation patterns (varying interval timing) can be utilized to more readily determine the appropriate delay times between current delivery in the specific vectors. Such an equation can be more readily derived by using the echo interface and will likely be exponential in nature. The exponent will be a different number during increases in heart rate that may occur with exercise. Such a change in the equation will require analysis of electromechanical relationships during exercise or inotropic stimulation. The device can autonomously derive this equation and if changes in the equation becomes necessary (evidence of increased dysynchrony) the DMS can alert the physician that a patient's clinical status has changed.

In another embodiment, measurements of cardiac performance such as a determination of inotropy (e.g. dZ/dt or SCP) can be made with impedance signals and serve to modify which equations are used to direct interval timing. These equations would have to be individualized and based on either data acquired with an echo interface or by historical values of time to peak impedance at different sets of interval timing under varying inotropic states.

In circumstances where impedance data is not able to be used at all the system can use an alternate means of optimizing timing that relies on assessment of a disparity index based on intracardiac electrograms (see below), or based on pre-determined defaults as depicted in step 11, FIG. 20. The AOA in this case would utilize measurements of TPI as to oversee the control system.

Disparity Indices of Intracardiac Electrograms

In an alternate embodiment, intracardiac electrograms derived from multi-site electrodes can be used for deriving a disparity index. The greater the disparity of intrinsic electrical activation patterns the more dysynchrony is present (METHOD AND APPARATUS FOR PROGRAMMING INTERVAL TIMING IN CRT DEVICES, application Ser. No. 10/779,162). The disparity index can be used in a closed loop system as a parameter for determining optimal CRT interval timing. Relative timing of various features of IEGM signals will describe dysynchronous activation patterns better than surface ECG. This is because IEGMs provide a window into activation patterns that appear fused on a surface ECG. Analysis of IEGM to derive a disparity index can include but is not limited to evaluation of relative onset of EGM deflection, time of peak and termination of EGM "R" waves, duration of EGM "R" waves.

In a non-CRT device, such a disparity index can trigger an alert to inform the physician that intracardiac electrogram signals are suggestive of dysynchrony and that an upgrade to a CRT device should be considered. Use of the can electrode in a non-CRT device will help incorporate electrogram data that represents left ventricular activation patterns. Any number of variables that reflect relative timing of depolarization in different vectors can be used to derive disparity indices for such an embodiment.

Matrix Optimization Method (MOM)

The descriptions herein relate mainly to conventional biventricular pacing systems and temporal relationships between dual site ventricular pacing stimuli. Resynchronization therapy may employ multiple electrodes for stimulation between and/or within the cardiac chambers. Optimal interval timing includes atrial-ventricular intervals (AVI) and possibly multi-site pacing with additional electrode pairs (VaVb) in addition to conventional biventricular electrodes (VrVl). AVI can be programmed based on equations described in the literature, AV optimization techniques using echo or intrinsically within the closed loop system. The details of the MOM are described in more detail above and in the parent patent application Ser. No. 10/779,162.

AV optimization using Impedance Data

Figure 24:
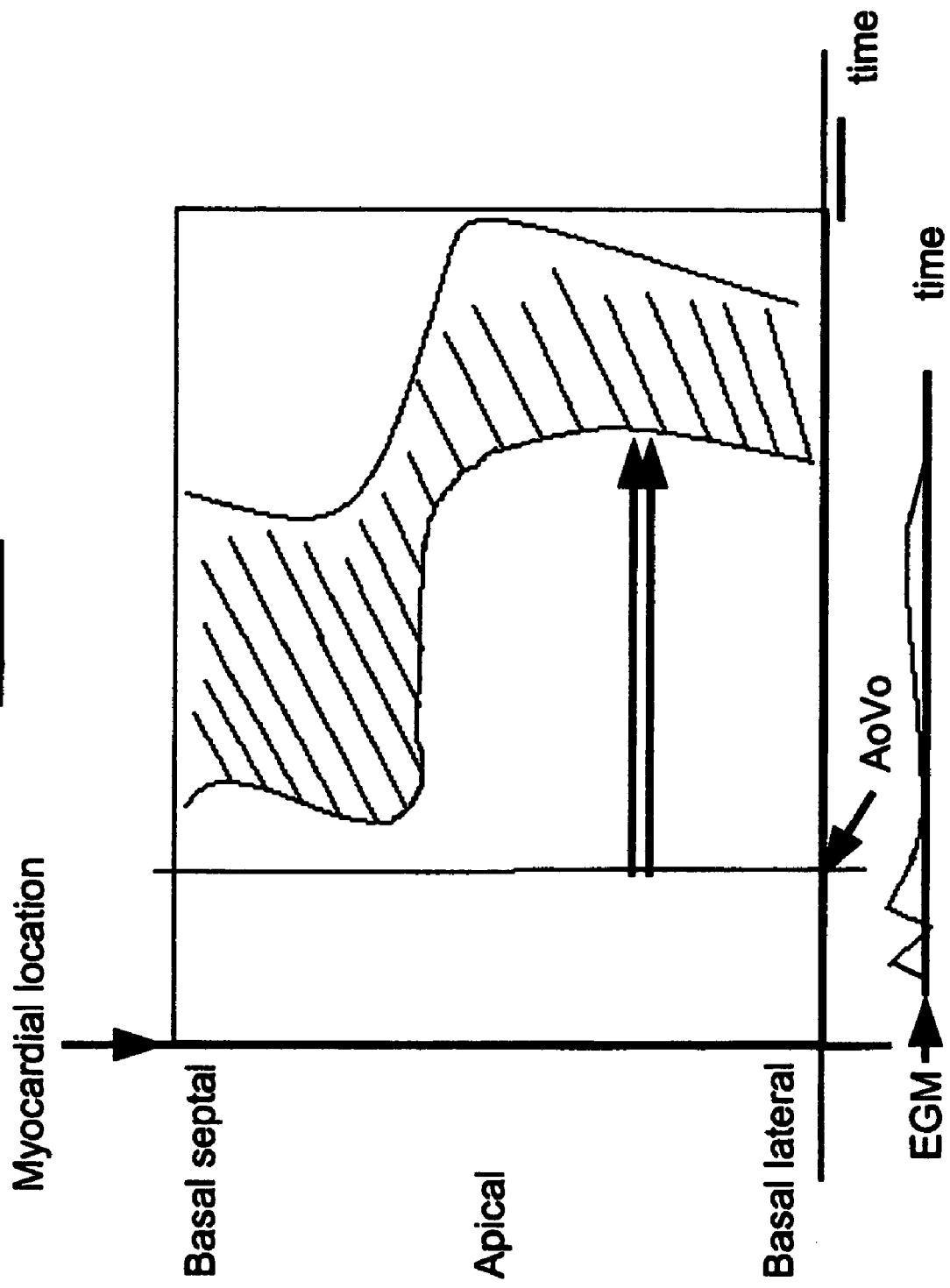
FIG. 24 is a picture of curved M mode data (General Electric) illustrating how delays in timing affect regional myocardial thickening.
Figure 25:
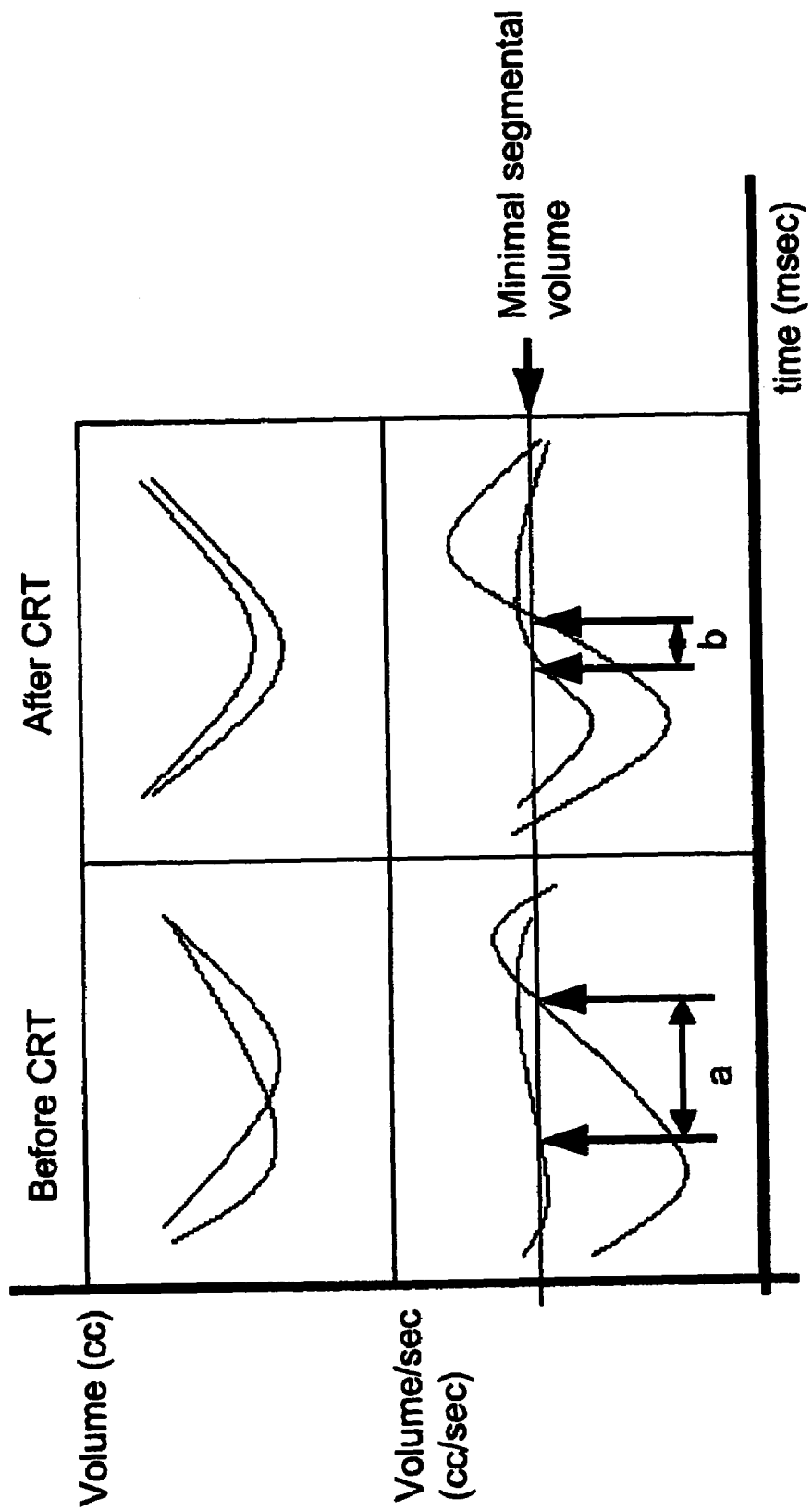
FIG. 25 illustrates how resynchronization can reduce or eliminate delays in regional myocardial thickening by analysis of charges in regional volume time curves (TomTec Imaging—Philips).

Impedance data can be utilized for AV optimization purposes as well. One method of achieving this can be by injecting current impulses during the cardiac cycle and determining end-diastole when the impedance value is at a minimum. Limitations in the application of such impedance data for AV optimization are several-fold. Onset of initial ventricular contraction should occur after maximal filling of the ventricular chambers. This will correspond to a time frame when trans-cardiac impedance is at a nadir. Dysynchronous hearts, however, have regional variations in mechanical end diastole. This has been demonstrated in the ultrasound literature. FIG. 24 demonstrates an ultrasound modality, curved M mode imaging. In this example one can visualize that specific myocardial segments begin contracting (regional end-diastole) after other segments. These delays can approach 500 milliseconds. If the impedance waveforms relate to myocardial segments with delayed contractility, AV optimization can occur after aortic valve closure. Ultrasonic imaging can demonstrate this by analysis of regional changes in volume as well. FIG. 25 depicts time to minimal regional volume using Philips three dimensional echocardiographic imaging before and after resynchronization.

In order to overcome these limitations adequately, one can use multiple impedance waveforms in a variety of vectors with summation averaging techniques. Alternatively, multipolar impedance data acquisition will more accurately reflect global changes during the cardiac cycle. Electrodes with vectors that traverse the atrial chambers or great vessels will potentially be 180 degrees out of phase with ventricular events and should not be utilized for data acquisition. Ideally, AV optimization should occur after inter- and intraventricular dysynchrony has been minimized. In this fashion, there will be more congruence between regionally obtained impedance waveforms.

An additional point is that for any changes in interval timing in one dimension, further modifications in interval timing will be needed in another dimension. For example, changes in VrVI may cause a change in the systolic ejection period, which necessitates adjustments in the AVI from the time of original programming. For this to occur dynamically, the MOM algorithm can be utilized (FIG. 26 and METHOD AND APPARATUS FOR PROGRAMMING INTERVAL TIMING IN CRT DEVICES, patent Ser. No. 10/779,162). By way of example, a three dimensional mathematical array can include several permutations of AVI, predetermined VrVI where EMCFI approaches unity, and several VaVb. The parameter which best describes Global Cardiac Performance (e.g. GCRP if signal integrity is ideal or peak dZ/dt if less than ideal) will be the one optimized using this methodology. Use of these modalities for fine-tuning interval timing will optimally optimize synchrony without the pitfalls of using regionally derived impedance data as to direct AV timing.

Prevention of Positive Feedback

In the event an impedance signal is misinterpreted in a significant fashion as a result of an unexpected disturbance (e.g. not cardiac translation) the Vital Control System will not be able to pace with interval timing that falls outside a pre-determined range of values. This range of values can be programmed using default intervals, based on echo interface or template data. The template data based on a specific individual's needs during a specified prior time frame will better serve the patient, unless some major change in the patient's underlying status occurs (infarction). The Automatic Optimization Algorithm is capable of detecting such a dramatic change acutely (with parameters of Global Cardiac Performance: dZ/dt, Z(peak), dZ'/dt, various integrals of Z(t) dt such as LCP,SCP) and on a more chronic basis. The parameters most applicable to chronic measurements are those incorporating measurements of thoracic fluid volume (pulmonary vascular congestion) such as Z offset, and GCRP (SLI× trans-pulmonic impedance). By these mechanisms a deleterious condition will be avoided.

Numerous modifications can be made to this invention without departing from its scope as defined in the appended claims. Implementation of individual embodiments described herein does not necessitate use of any specific inventions described in this patent application concurrently.

I claim:

1. A method of programming a cardiac resynchronization therapy (CRT) device comprising:
   determining a control parameter associated with dynamic intracardiac impedance data of a patient;
   determining if said control parameter is acceptable; and
   setting an operational parameter of said CRT based on said control parameter;
   wherein said control parameter is determined by measuring the impedances along several vectors and determining said control parameter from these vectors.

2. The method of claim 1 wherein impedances are measured during several cardiac cycles using techniques of ensemble averaging.

3. The method of claim 2 wherein said control parameter is determined by summation averaging of individually derived parameters.

4. The method of claim 1 wherein acceptable control parameters are determined using multivariate statistical analysis techniques.

5. The method of claim 1 wherein said acceptable control parameters are determined by comparison to waveforms obtained previously from the patient.

6. The method of claim 1 wherein said CRT applies excitation signals to the different electrodes and analysis of said control parameter is used to direct the timing of said excitation signals to eliminate dysynchrony between or within said cardiac chambers.

7. A programming system comprising:
a cardiac resynchronization therapy (CRT) device applying therapy to a patient based on a plurality of operational parameters;
a parameter detector that detects a control parameter related to the dynamic intrathoracic impedance of the patient;
a parameter evaluator that determines if said control parameter is acceptable;
a controller that uses said control parameter to set said operational parameters based on said control parameter, if said control parameter is found acceptable;
a programmer, said parameter detector and said parameter evaluator being disposed in said programmer; and
wherein said parameter detector and said parameter evaluator are disposed in said CRT.

8. An implantable cardiac resynchronization therapy (CRT) device comprising:
a sensor that senses intrinsic cardiac events and generates corresponding sensing signals;
an excitation generator generating excitation signals for different locations of the heart in response to commands;
a controller generating said commands in accordance with a plurality of operational parameters dependent on said sensing signals;
a parameter generator generating a control parameter dependent on a thoracic impedance of the patient; and
a parameter evaluator that determines if said control parameter is acceptable based on a set of preset criteria;
wherein said control parameter is used by the controller to reduce dysynchrony between or within the cardiac chambers; and
wherein said control parameter is used by the controller to optimize cardiac performance by maximizing cardiac output.

9. The implantable CRT of claim 8 wherein said parameter generator can acquire impedance data using data sampling methodologies selected to reduce costs to the system and reduce the affect of uncontrollable inputs and measurement errors.

10. The implantable CRT of claim 8 wherein said controller delineates event timing and extrapolates this to intracardiac electrograms for reference purposes.

11. The implantable CRT of claim 8 wherein said controller is adapted to modify pacing parameters, altering tachyarrhythmia therapies and relaying relevant clinical variables to a remote location when changes in clinical status occurs.

12. A method of stimulating a patient's heart comprising:
generating stimulation signals to the heart;
measuring a thoracic impedance of the heart by performing measurements between several implanted electrode pairs and combining said measurements to determine said impedance;
detecting a dysynchrony between a right and a left chamber from said impedance; and
adjusting the timing of said stimulation signals to reduce said dysynchrony.

13. The method of claim 12 wherein said thoracic impedance is determined by performing measurements between several implanted electrode pairs and selecting an optimal measurement.

14. A method of programming a cardiac resynchronization therapy (CRT) device comprising:
determining a control parameter associated with dynamic intracardiac impedance data of a patient;
determining if said control parameter is acceptable; and
setting an operational parameter of said CRT device based on said control parameter;
wherein acceptable control parameters are determined using multivariate statistical analysis techniques.

15. An implantable cardiac resynchronization therapy (CRT) device comprising:
a sensor that senses intrinsic cardiac events and generates corresponding sensing signals;
an excitation generator generating excitation signals for different locations of the heart in response to commands;
a controller generating said commands in accordance with a plurality of operational parameters dependent on said sensing signals;
a parameter generator generating a control parameter dependent on a thoracic impedance of the patient; and
a parameter evaluator that determines if said control parameter is acceptable based on a set of preset criteria;
wherein said control parameter is used by the controller to optimize cardiac performance by maximizing cardiac output.

* * * * *